US006437105B1

(12) United States Patent
Priebe et al.

(10) Patent No.: US 6,437,105 B1
(45) Date of Patent: Aug. 20, 2002

(54) METHODS AND COMPOSITIONS FOR THE MANUFACTURE OF HIGHLY POTENT ANTHRACYCLINE-BASED ANTITUMOR AGENTS

(75) Inventors: Waldemar Priebe, Houston, TX (US); Teresa Przewloka, Acton, MA (US); Izabela Fokt, The Woodlands, TX (US); Yi-He Ling; Roman Perez-Soler, both of New York, NY (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/432,190

(22) Filed: Nov. 2, 1999

Related U.S. Application Data

(60) Provisional application No. 60/106,730, filed on Nov. 2, 1998.

(51) Int. Cl.$^7$ .............................................. C07H 15/24
(52) U.S. Cl. ....................................................... 536/6.4
(58) Field of Search .......................................... 536/6.4

(56) References Cited

U.S. PATENT DOCUMENTS

| | | | | |
|---|---|---|---|---|
| 4,263,428 A | * | 4/1981 | Apple et al. .................. | 536/6.4 |
| 4,345,070 A | * | 8/1982 | Suarato et al. ............... | 536/6.4 |
| 4,438,105 A | * | 3/1984 | Suarato et al. ............... | 424/180 |
| 5,698,528 A | * | 12/1997 | Kawauchi et al. ............ | 536/6.4 |

OTHER PUBLICATIONS

Bodley et al., "DNA topoisomerase II–mediated interaction of duxorubicin and dauorubicin congeners with DNA," *Cancer Res.*, 49:5969–5978, 1989.*
Booser and Hortobagyi, "Anthracycline Antibiotics in Cancer Therapy. Focus on Drug Resistance," *Drugs*, 47:223–258, 1994.*
Bradley et al., "Mechanism of multidrug resistance," *Biochem. Biophys. Acta.*, 948:87–128, 1988.*
Capranico et al., "Sequence–Selective topoisomerase ii inhibition by anthracycline derivatives in sv40 dna: relationship with dna binding affinity and cytotoxicity," *Biochem*, 29:562–569, 1990.*
Chaires et al., "Structure–based design of a new bisintercalating anthracycline antibiotic," *J. Med. Chem.*, 40:261–266, 1997.*
Fojo et al., "Expression of a multidrug–resistance gene in human tumors and tissues," *Proc. Natl. Acad. Sci. USA.*, 84:265–269, 1987.*
Ganapathi, et al., "N–Benzyladriamycin–14–valerate versus progressively doxorubicin–resistant murine tumors: cellular pharmacology and characterisation of cross–resistance in vitro and in vivo," *Br. J. Cancer*, 60:819–826, 1989.*
Gao et al., "Substitutions and C2' of daunosamine in the anticancer drug daunorubicin alter its DNA–binding sequence specificity," *Eur. J. Biochem.*, 240:331–335, 1996.

Gros et al., "Isolation and expression of a complementary DNA that confers multidrug resistance," *Nature*, 323:728–731, 1986.
Hu et al., "Structure of a DNA–Bisdaunomycin Complex," *Biochemistry*, 36:5940–5946, 1997.
Israel et al., "Amelioration of adriamycin toxicity through modification of drug–DNA binding properties," *Cancer Treat Rev.*, 14:163–167, 1987.
Israel et al., "Comparative uptake and retention of adriamycin and N–benzyladriamycin–14–valerate in human CEM leukemic lymphocyte cell structures," *Cancer Chemother. Pharmacol.*, 25:177, 1989.
Katsumata et al., "Prevention of breast tumor development in vivo by down–regulation of the p185$^{neu}$ receptor," *Nature Med.*, 1:644–648, 1995.
Leng et al., "Base specific and regioselective chemical cross–linking of daunorubicin to dna," *J. Am. Chem. Soc.*, 118:4731–4738, 1996.
Lown, Anthracycline and Anthracenedione–Based Anticancer Agents, Bioactive Molecules, vol. 6, Elsevier Science Publishing Company, Inc., 1988.
Lown, "Targeting the DNA Minor Groove for Control of Biological Function: Progress, Challenges and Prospects", *Chemtracts—Org. Chem.*, 6:205–237, 1993
Marchini et al., "Sequence–specific DNA interactions by novel alkylating anthracycline derivatives," *Anti–Cancer Drug Design*, 10:641–653, 1995.
Norris et al., "Expression of the gene for multidrug–resistance–associated protein and outcome in patients with neuroblastoma", *N. Engl. J. Med*, 334:231–238, 1996.
Perez–Soler et al., "Development of Liposomal–Annamycin," Abstract 035 Presented at the ACS meeting, Mar. 24–28, 1996.
Priebe et al., "3'–Hydroxyesorubicin halogenated at C–2," *J. Antibiot*, 45:386–393, 1992.
Priebe et al., "Exploration of Target–Governed Design of Anthracyclines," Abstract 016 Presented at the ACS meeting, Mar. 24–28, 1996.
Priebe et al., "Photoaffinity Labeling of P–Glycoprotein and Its Inhibition by Charged and Uncharged Anthracyclines," Abstract 049 Presented at the ACS meeting, Mar. 24–28, 1996.
Priebe et al., "Removal of the basic center from doxorubicin partially overcomes multidrug resistance and decreases cardiotoxicity," *Anti–Cancer Drugs*, 4:37–48, 1993.
Priebe W, "Anthracycline Antibiotics. New Analogues, Methods of Delivery, and Mechanisms of Action", ACS Symposium Series 574, 1995.

(List continued on next page.)

Primary Examiner—Elli Peselev
(74) *Attorney, Agent, or Firm*—Fulbright & Jaworski LLP

(57) ABSTRACT

The present invention discloses new and novel substituted anthracyclines having a three ring system or other DNA binding moieties. These congeners show high activity in vitro against several tumor cell lines. The invention also describes anthracycline-based DNA alkylators.

15 Claims, 9 Drawing Sheets

OTHER PUBLICATIONS

Priebe W. "Mechanism of Action–Governed Design of Anthracycline Antibiotics: A "Turn–Off/Turn–On" Approach," *Current Pharmaceutical Design*, 1:51–68, 1995.

Robinson et al., "Binding of Two Novel Bisdaunorubicins to DNA Studies by NMR Spectroscopy," *Biochemistry*, 36:8663–8670, 1997.

Rubinstein et al., "Comparison of In Vitro Anti–Cancer–Drug–Screening Data Generated with A Tetrazolium Assay Versus a Protein Assay Against a Diverse Panel of Human Tumor Cell Lines," *J. Nat'l. Cancer Inst.*, 82:1113–1120, 1990.

Traganos et al., "Effects of new N–alkyl analogues of adriamycin on in vitro survival and cell cycle progression of L1210 cells," *Cancer Res.*, 45:6273–6279, 1985.

* cited by examiner

R=H; Daunorubicin
R=OH; Doxorubicin

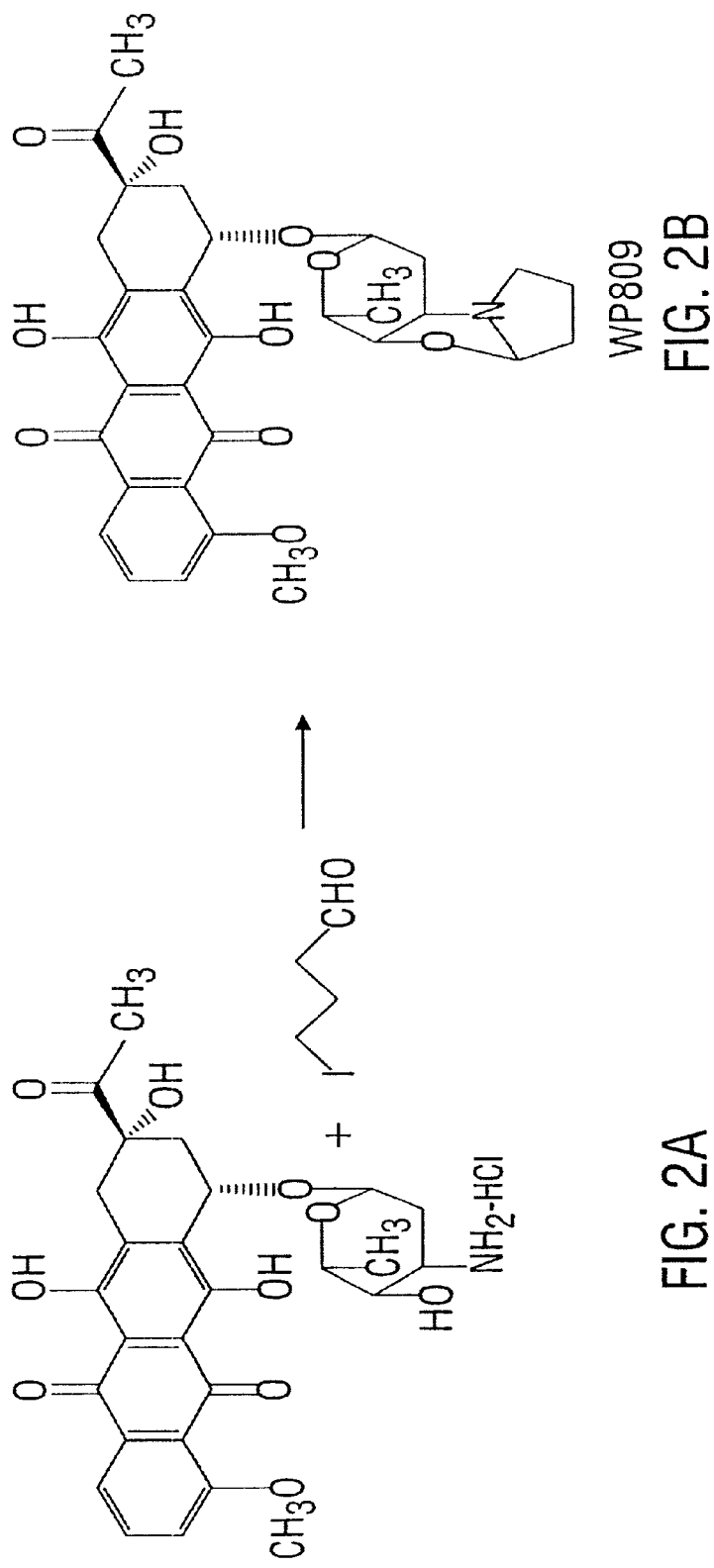

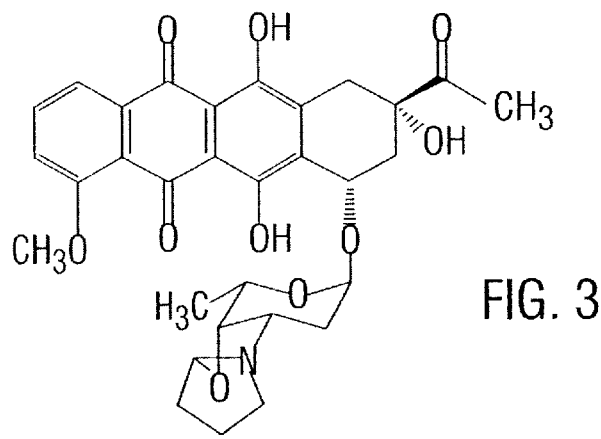
WP809
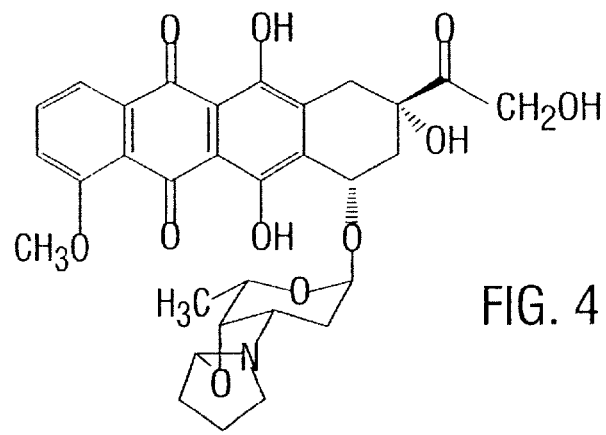
WP836
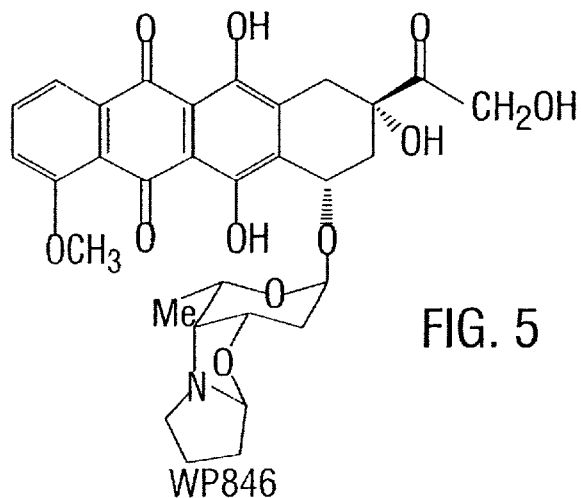
FIG. 5
WP846

WP851

WP840

WP885

1-Ribo analog of WP809

R_L - leaving group like I, OMs, OTs

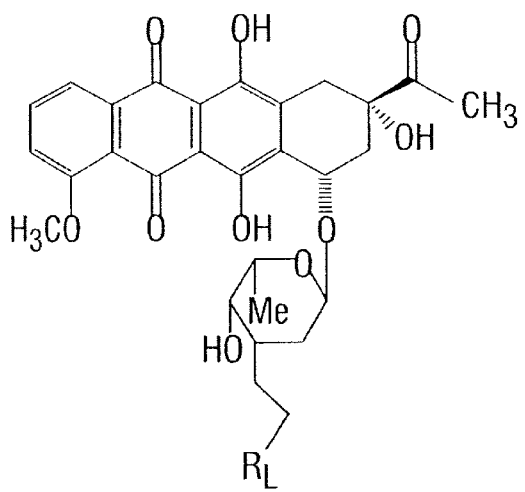
$R_L$ - leaving group like I, OMs, OTs
FIG. 12A
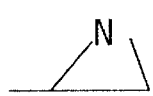
aziridine
oxirane
thiirane
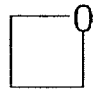
oxetane
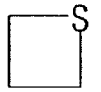
thietane
FIG. 12B    FIG. 12C    FIG. 12D    FIG. 12E    FIG. 12F
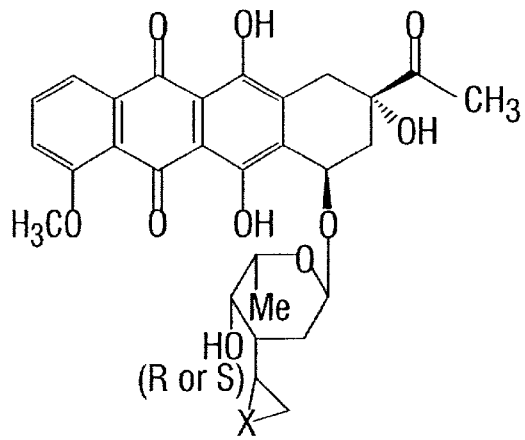
X = O or NH
FIG. 13

METHODS AND COMPOSITIONS FOR THE MANUFACTURE OF HIGHLY POTENT ANTHRACYCLINE-BASED ANTITUMOR AGENTS

The present application is a continuation-in-part of co-pending U.S. patent application Ser. No. 60/106,730, filed Nov. 2, 1998. The entire text of the above-referenced disclosure is specifically incorporated by reference herein without disclaimer.

The U.S. Government owns rights in the present invention pursuant to National Institute of Health grants numbered CA55270 and CA50320.

BACKGROUND OF THE INVENTION

1. Field of the Invention

The present invention relates generally to the treatment of cancer. More particularly, it concerns novel compounds useful for chemotherapy, methods of synthesis of these compounds and methods of treatment employing these compounds. The novel compounds are substituted anthracyclines having a three ring system related to anthracyclines such as daunorubicin, idarubicin, epirubicin, and doxorubicin which are known to have antitumor activity.

2. Description of Related Art

Resistance of tumor cells to the killing effects of chemotherapy is one of the central problems in the management of cancer. It is now apparent that at diagnosis many human tumors already contain cancer cells that are resistant to standard chemotherapeutic agents. Spontaneous mutation toward drug resistance is estimated to occur in one of every $10^6$ to $10^7$ cancer cells. This mutation rate appears to be independent of any selective pressure from drug therapy, although radiation therapy and chemotherapy may give rise to additional mutations and contribute to tumor progression within cancer cell populations (Goldie et al., 1979; Goldie et al., 1984; Nowell, 1986). The cancer cell burden at diagnosis is therefore of paramount importance because even tumors as small as 1 cm ($10^9$ cells) could contain as many as 100 to 1,000 drug-resistant cells prior to the start of therapy.

Selective killing of only the tumor cells sensitive to the drugs leads to an overgrowth of tumor cells that are resistant to the chemotherapy. Mechanisms of drug resistance include decreased drug accumulation (particularly in multi-drug resistance), accelerated metabolism of the drug and other alterations of drug metabolism, and an increase in the ability of the cell to repair drug-induced damage (Curt et al., 1984; and Kolate, 1986). The cells that overgrow the tumor population not only are resistant to the agents used but also tend to be resistant to other drugs, many of which have dissimilar mechanisms of action. This phenomenon, called pleiotropic drug resistance or multi-drug resistance (MDR), may account for much of the drug resistance that occurs in previously treated cancer patients. The development of drug resistance is one of the major obstacles in the management of cancer. One of the traditional ways to attempt to circumvent this problem of drug resistance has been combination chemotherapy.

Combination drug therapy is the basis for most chemotherapy employed to treat breast, lung, and ovarian cancers as well as Hodgkin's disease, non-Hodgkin's lymphomas, acute leukemias, and carcinoma of the testes. Combination chemotherapy uses the differing mechanisms of action and cytotoxic potentials of multiple drugs.

Although combination chemotherapy has been successful in many cases, the need still exists for new anti-cancer drugs. These new drugs could be such that they are useful in conjunction with standard combination chemotherapy, or these new drugs could attack drug resistant tumors by having the ability to kill cells of multiple resistance phenotypes.

A drug that exhibits the ability to overcome multiple drug resistance could be employed as a chemotherapeutic agent either alone or in combination with other drugs. The potential advantages of using such a drug in combination with chemotherapy would be the need to employ fewer toxic compounds in the combination, cost savings, and a synergistic effect leading to a treatment regime involving fewer treatments.

The commonly used chemotherapeutic agents are classified by their mode of action, origin, or structure, although some drugs do not fit clearly into any single group. The categories include alkylating agents, anti-metabolites, antibiotics, alkaloids, and miscellaneous agents (including hormones). Agents in the different categories have different sites of action.

Antibiotics are biologic products of bacteria or fungi. They do not share a single mechanism of action. The anthracyclines daunorubicin and doxorubicin (DOX) are some of the more commonly used chemotherapeutic antibiotics. The anthracyclines achieve their cytotoxic effect by several mechanisms, including inhibition of topoisomerase II; intercalation between DNA strands, thereby interfering with DNA and RNA synthesis; production of free radicals that react with and damage intracellular proteins and nucleic acids; chelation of divalent cations; and reaction with cell membranes. The wide range of potential sites of action may account for the broad efficacy as well as the toxicity of the anthracyclines (Young et al., 1985).

The anthracycline antibiotics are produced by the fungus *Streptomyces peuceitius* var. *caesius*. Although they differ only slightly in chemical structure, daunorubicin has been used primarily in the acute leukemias, whereas doxorubicin displays broader activity against human neoplasms, including a variety of solid tumors. The clinical value of both agents is limited by an unusual cardiomyopathy, the occurrence of which is related to the total dose of the drug; it is often irreversible. In a search for agents with high antitumor activity but reduced cardiac toxicity, anthracycline derivatives and related compounds have been prepared. Several of these have shown promise in the early stages of clinical study, and some, like epirubicin and idarubicin, are used as drugs. Epirubicin outsells doxorubicin in Europe and Japan, but it is not sold in the U.S.

The anthracycline antibiotics have tetracycline ring structures with an unusual sugar, daunosamine, attached by glycosidic linkage. Cytotoxic agents of this class all have quinone and hydroquinone moieties on adjacent rings that permit them to function as electron-accepting and donating agents. Although there are marked differences in the clinical use of daunorubicin and doxorubicin, their chemical structures differ only by a single hydroxyl group on C14. The chemical structures of daunorubicin and doxorubicin are shown in FIG. 1.

Doxorubicin's broad spectrum of activity against most hematological malignancies as well as carcinomas of the lung, breast, and ovary has made it a leading agent in the treatment of neoplastic disease (Arcamone, 1981; Lown, 1988; Priebe, 1995). Since the discovery of daunorubicin and doxorubicin (FIG. 1), the mechanistic details of the antitumor activity of anthracycline antibiotics have been actively investigated (Priebe, 1995a; Priebe, 1995b; Booser, 1994).

Unfortunately, concomitant with its antitumor activity, DOX can produce adverse systemic effects, including acute myelosuppression, cumulative cardiotoxicity, and gastrointestinal toxicity (Young et al., 1985). At the cellular level, in both cultured mammalian cells and primary tumor cells, DOX can select for multiple mechanisms of drug resistance that decrease its chemotherapeutic efficacy. These mechanisms include P-gp-mediated MDR and MPR-rediated MDR, characterized by the energy-dependent transport of drugs from the cell (Bradley et al., 1988), and resistance conferred by decreased topoisomerase II activity, resulting in the decreased anthracycline-induced DNA strand scission (Danks et al., 1987; Pommier et al, 1986; Moscow et al., 1988.

Among the potential avenues of circumvention of systemic toxicity and cellular drug resistance of the natural anthracyclines is the development of semi-synthetic anthracycline analogues which demonstrate greater tumor-specific toxicity and less susceptibility to various forms of resistance.

SUMMARY OF THE INVENTION

The present invention seeks to overcome drawbacks inherent in the prior art by providing compositions of agents that display increased cytotoxicity when compared with doxorubicin and can prevent and/or overcome multi-drug resistance and exhibit reduced cardiotoxicity. This invention involves novel compounds that have utility as antitumor and/or chemotherapeutic drugs, methods of synthesizing these compounds and methods of using these compounds to treat patients with cancer. The invention is generally based on the discovery that anthracycline derivatives that have ring groups or other groups attached to their sugar moiety have a surprisingly strong ability to kill tumor cells. In one aspect, the invention relates to compounds that can form an alkyl bond with DNA via formaldehyde mediated cross-linking.

To design novel anticancer drugs with improved targeting of DNA, the inventors have studied in depth how anthracyclines interact with DNA. First, their studies of the energetics of anthracyclines binding to DNA and analysis of the x-ray diffraction data of monomeric anthracyclines complexes with DNA oligonucleotides led to the rational design of DNA-bisintercalating drugs. Second, the inventors' studies of formaldehyde-mediated crosslinking of anthracyclines with DNA, which demonstrated the regioselectivity and base specificity of that process, led us to prepare novel drugs designed to form covalent bonds with N2 guanine of DNA. In vitro evaluation identified DNA-crosslinking anthracyclines WP809 and WP836 as unusually potent cytotoxic agents.

New anthracyline-based agents designed to interact and crosslink with DNA have been synthesized. Some of these analogs contain unique three ring system which is relatively stable. Synthesized compounds displayed activity significantly higher than that of parental daunorubicin or doxorubicin. In brief, in vitro the compound WP836 derived from doxorubicin was 500- to 25,000-fold more potent than doxorubicin in test performed in several cell lines. Similarly, the increased activity was also noticed for analog WP809 obtained from daunorubicin. Other analogs were also designed and synthesized. Observed activity and high potency indicate that the primary mechanism of action of these analogs is different from doxorubicin and daunorubicin.

The substituted anthracyclines having a three ring system are exemplified by those anthracyclines found in FIGS. 3–9.

These actions produced substituted anthracyclines having a three ring system which exhibit activity substantially different from the activities of doxorubicin or daunorubicin. These compounds are active against doxorubicin resistant tumors and/or are more cytotoxic than doxorubicin against sensitive tumors, and the mechanism probably relates to the sequence-governed, base-specific alkylation of DNA. Other substituted anthracyclines are exemplified in FIGS. 11, 12, 14, and 15.

In some specific embodiments, the substituted anthracycline compounds have the general formula:

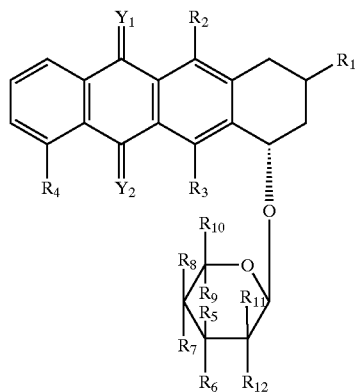

wherein: $R^1$ denotes any suitable group or combination of groups to form a nucleic acid intercalator or binding compound, including but not limited to hydrogen (—H) group, a hydroxyl group (—OH), a methoxy group (—OCH$_3$), an alkoxy group having 1–20 carbon atoms, an alkyl group having 1–20 carbon atoms, an aryl group having 1–20 carbon atoms, a fatty acyl group having the general structure —O—CO(CH$_2$)$_n$CH$_3$, wherein n=an integer from 1 to about 20, or a fatty acyl group having the general structure —O—CO(CH2)$_1$(CH=CH)$_m$(CH2)$_n$CH$_3$, wherein 1 is an integer between 1 to 3, m is an integer between 1 and about 6, and n is an integer between 1 to about 9; each of $R^2$ and $R^3$ is, independently of the other, a hydrogen (—H) group, a hydroxyl group (—OH), a methoxy group (—OCH$_3$) or a double bonded oxygen moiety; $R^4$ is a hydrogen (—H) group, a hydroxyl group (—OH), a methoxy group (—OCH$_3$) or a halide; each of $Y^1$ and $Y^2$ is, independently of the other, a hydrogen (—H) group; a hydroxyl group (—OH); a methoxy group (—OCH$_3$); or a double bonded oxygen, sulphur, or nitrogen group; $R^5$–$R^{12}$ are, independently, —H, —OH, a halide, —OR$^{13}$, —SH, —SR$^{13}$, —NH$_2$, —NHR$^{13}$, —N(R$^{13}$)$_2$, and R can additionally be a saccharide, with the proviso that both of $R^6$ and $R^7$ or both of $R^5$ and $R^8$ or both of $R^5$ and $R^{11}$ or both of $R^6$ and $R^{12}$ are involved in forming a three ring structure or either of $R^5$ and $R^6$ is independently a mercapto-haloalkyl group or ether alkyl group containing easy leaving groups [halogen like iodine or sulfonate esters (—OSO2R) like mesyl or tosyl] or ether alkyl group containing aziridine, oxirane, thiirane, oxetane, thietane rings; and $R^{13}$ is a hydrogen (—H) group, a hydroxyl group (—OH), a methoxy group (—OCH$_3$), an alkoxy group having 1–20 carbon atoms, an alkyl group having 1–20 carbon atoms, an aryl group having 1–20 carbon atoms, a fatty acyl group having the general structure —O—CO(CH2)$_n$CH$_3$, wherein n=an integer from 1 to about 20, or a fatty acyl group having the general structure —O—CO(CH2)$_1$(CH=CH)$_m$(CH2)$_n$CH3, wherein 1 is an integer between 1 to 3, m is an integer between 1 and about 6, and n is an integer between 1 to about 9.

Certain specific embodiments of the anthracyclines of the invention are shown in FIGS. 3–9 and FIGS. 12–15.

In the specific methods disclosed in this patent, iodobutyraldehyde is employed to form the three ring structure, as described in Example 1 and shown in FIG. 2. However, a variety of longer, shorter, or different halogenated aldehydes may be employed in the place of the iodobutyraldehyde in the general procedure to cause variations in the three ring structure. Exemplary three ring structures created by the use of iodobutyraldehyde are shown in FIG. 10. Such structures may be modified by varying the starting halogenated aldehydes to have additional atoms in their rings, different atoms in the place of the nitrogen and oxygens therein, and different side groups. Three ring structures formed in this manner may, in the broadest embodiments of the invention be attached to any suitable nucleic acid intercalating group or binding group that will bring the alkylating function of the three ring group into proximity with DNA, including, but not limited to the anthracyclines disclosed herein.

Other anthracycline-based DNA alkylators are also described herein and some examples are shown in FIGS. 12–15 and their method of synthesis is described herein.

The present application also comprises methods of preparing anthracyclines. In devising the synthetic schemes and compounds of the present invention, the inventors have created a variety of novel compounds. These compounds are described elsewhere in the specification and figures, and are given "WP" numbers. The structure of a compound designated with a "WP" number is ascertainable by reviewing the specification and figures. Exemplary specific compounds that are encompassed by the invention are WP809, WP836, WP846, WP851, WP840, and WP885.

The invention also considers methods of treating a patient with cancer, comprising administering to the patient a therapeutically effective amount of the contemplated substituted anthracycline compounds and therapeutic kits comprising, in suitable container means, a pharmaceutically acceptable composition comprising the contemplated substituted anthracycline compounds.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2. Synthesis of WP809

FIG. 3. WP809

FIG. 4. WP836

FIG. 5. WP846

FIG. 12. An exemplary compound of the present invention, along with exemplary structures that can be part of the compound.

FIG. 13. Exemplary compounds of the present invention.

DESCRIPTION OF ILLUSTRATIVE EMBODIMENTS

The present invention provides new and novel DNA intercalating agents. These agents are substituted anthracyclines having a three ring system. These compounds show high activity against resistant tumors and cells. A novel approach of the invention produces compounds that are as active or more so than the parent compounds. Furthermore, the inventors' discovery is also for the design of effective DNA-binding substituted anthracyclines having a three ring system.

Figure 1:
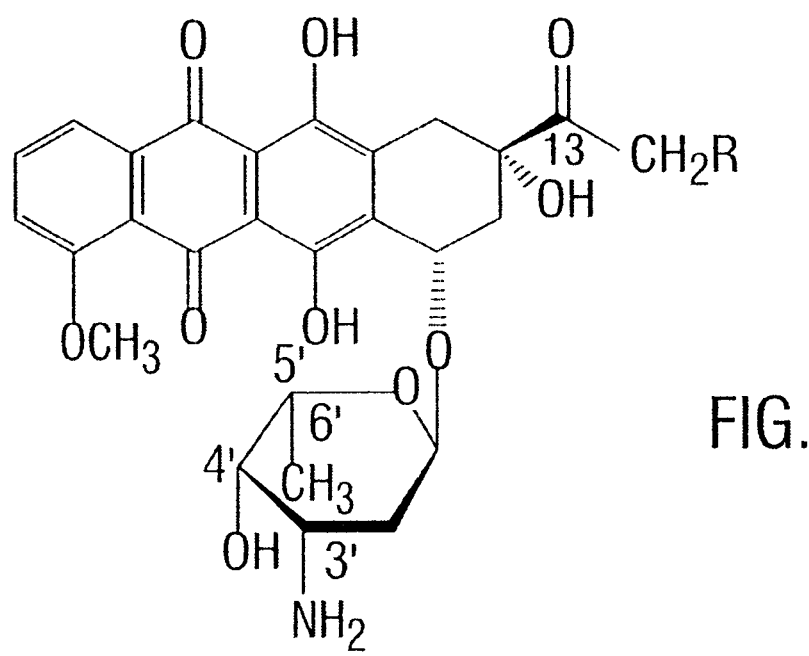
FIG. 1. Structure of Doxorubicin and Daunorubicin
Figure 6:
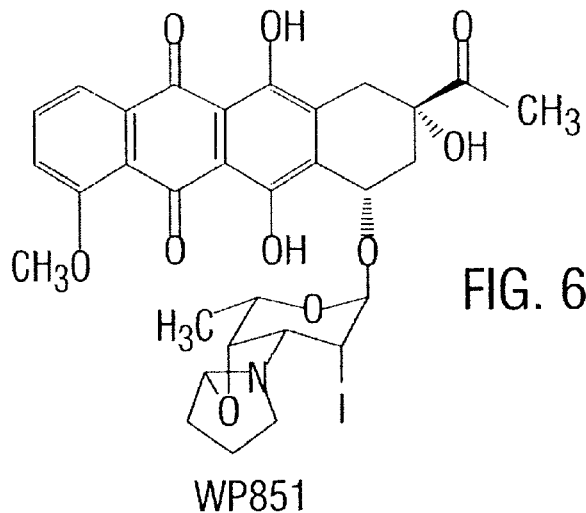
FIG. 6. WP851
Figure 7:
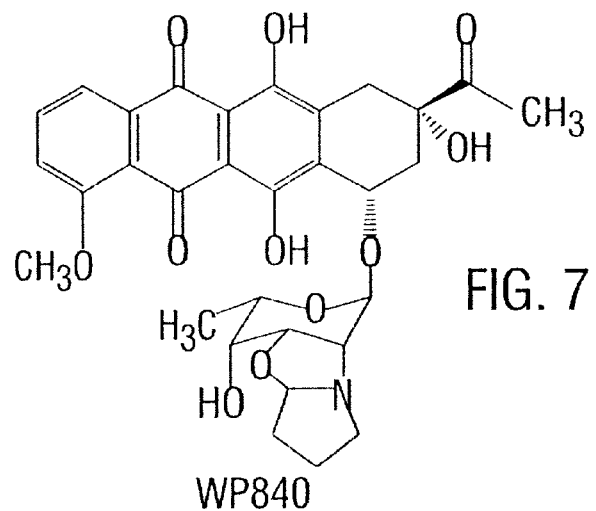
FIG. 7. WP840
Figure 8:
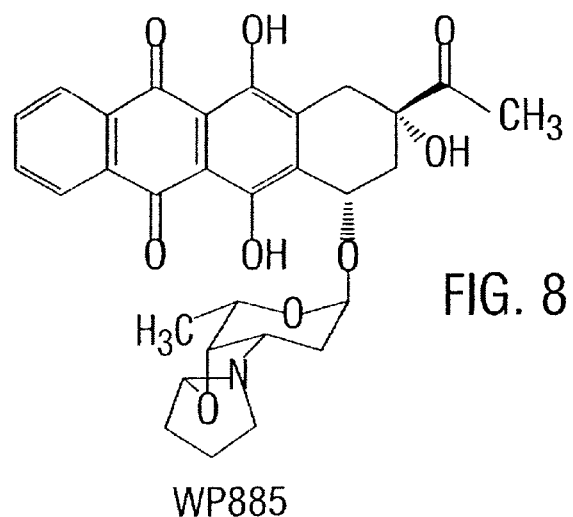
FIG. 8. WP885

The anthracycline compounds have a tetracycline ring structure with sugars attached by a glycosidic linkage. Cytotoxic agents of this class have quinone and hydroquinone moieties that permit them to function as electron-accepting and electron donating agents. Doxorubicin and daunorubicin are examples of compounds of this class (FIG. 1). These compounds act by intercalating with DNA. Examples of exemplary anthracyclinones and anthracyclines are given in Table 1.

TABLE 1

List of Exemplary anthracyclinones and anthracyclines.

Anthracyclinones

Rhodomycinone
Isorhodomycinone
Pyrromycinone
4-Demethoxydaunomycinone
4-Demethoxyadriamycinone
Daunomycinone
Adriamycinone
Anthracyclines Daunorubicin
Doxorubicin
Epirubicin
Idarubicin
Pyrromycin
Aclacinamycine
Isorhodomycine
Carminomycine
Doxorubicinc 14-esters:

Doxorubicin 14-acetate
Doxorubicin 14-propionate
Doxorubicin 14-octanoate
Doxorubicin 4-benzoate
Doxorubicine 14-phenylacetate
4'-Epidaunorubicin
4'-Epidoxorubicin
4'-Iododaunorubicin
4'-Iododoxorubicin
4'-Deoxydaunorubicin
4'-Deoxydoxorubicin
3'-Hydroxydaunorubicin
3'-Hydroxydoxorubicin
4-Demethoxydaunorubicin
4-Demethoxydoxorubicin
4'-Epi-4-demethoxydaunorubicin
4'-Epi-4-demethoxydoxorubicin Exemplary specific structures of the three ring portion of the substituted anthracyclines are found in FIG. 10.

Following long-standing patent law convention, the words "a" and "an", when used in the specification including the claims, denotes one or more.

"Aryl" may be a phenyl group, unsubstituted or substituted with a nitro, carboxy, sulfonic acid, hydroxy, oxyalkyl, or halide.

The term "saccharide" includes oxidized, reduced or substituted saccharides. Saccharides of this invention include, but are not limited to, ribose, arabinose, xylose, lyxose, allose, altrose, glucose, mannose, fructose, gulose, idose, galactose, talose, ribulose, sorbose, tagatose, gluconic acid, glucuronic acid, glucaric acididuronic acid rhamnose, fucose, N-acetyl glucosamine, N-acetyl galactosamine, N-acetyl neuraminic acid, sialic acid, derivatives of saccharides such as acetals, amines, and phosphorylated sugars, oligosaccharides, as well as open chain forms of various sugars, and the like.

An individual skilled in the art of organic synthesis in light of the present disclosure is able to prepare a large variety of substituted sugars and substituted anthracyclines having a three ring system which are expected to have chemotherapeutic activities and may be used in the treatment of cancer and/or other diseases. Exemplary substituted anthracyclines having a three ring system of the present invention are WP809, WP836, WP846, WP851, WP840, and WP885 (FIGS. 3–9). Such specific substituted anthracyclines having a three ring system have been synthesized by the inventors and have been analyzed and the structure confirmed by NMR and elemental analysis. The methods of the present application enable one of skill in the art to synthesize these compounds and many other related compounds without undue experimentation.

The present discoveries may be utilized in conjunction with certain techniques that are well-known in the biological arts and that are further described in the following sections.

Pharmaceutical Compositions

The antitumor compounds of this invention can be administered to kill tumor cells by any method that allows contact of the active ingredient with the agent's site of action in the tumor. They can be administered by any conventional methods available for use in conjunction with pharmaceuticals, either as individual therapeutically active ingredients or in a combination of therapeutically active ingredients. They can be administered alone but are generally administered with a pharmaceutically acceptable carrier selected on the basis of the chosen route of administration and standard pharmaceutical practice.

Aqueous compositions of the present invention will have an effective amount of anthracycline to kill or slow the growth of cancer cells. Further the potential recognition of genes can be accomplished by the synthesis of substituted anthracyclines having a three ring system or other chemical moeity with specific structures that allow for the recognition of specific parts of DNA. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

A. Parenteral Administration

The active compounds will often be formulated for parenteral administration, e.g., formulated for injection via the intravenous, intramuscular, subcutaneous, or even intraperitoneal routes. The preparation of an aqueous composition that contains an anthracycline of the present invention as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some forms, it will be desirable to formulate the novel compounds in salt form, generally to improve the solubility and bioavailability and to provide an active drug form more readily assimilated. As used herein, the term "pharmaceutically acceptable salt" refers to compounds which are formed from acidifying a substituted anthracycline solution with suitable physiologically tolerated acids. Suitable physiologically tolerated acids are organic and inorganic acids, such as hydrochloric acid, sulfuric acid, phosphoric acid, acetic acid, citric acid, oxalic acid, malonic acid, salicylic acid, maleic acid, methane sulfonic acid, isothionic acid, lactic acid, gluconic acid, glucuronic acid, amidosulfuric acid, benzoic acid, tartaric acid and pamoaic acid. Typically, such salt forms of the active compound will be provided or mixed prior to use.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts and which are formed with inorganic acids such as, for example, hydrochloric or phosphoric acids, or such organic acids as acetic, oxalic, tartaric, mandelic, and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in creams and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

B. Oral Administration

In certain embodiments, active compounds may be administered orally. This is contemplated for agents which are generally resistant, or have been rendered resistant, to proteolysis by digestive enzymes. Such compounds are contemplated to include all those compounds, or drugs, that are available in tablet form from the manufacturer and derivatives and analogues thereof.

For oral administration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Upon formulation, the compounds will be administered in a manner compatible with the dosage formulation and in such amount as is therapeutically effective. The formulations are easily administered in a variety of dosage forms, such as those described below in specific examples.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Synthesis of Exemplary Substituted Anthracyclines Having a Three Ring System

General Procedure for Making Substituted Anthracyclines Having a Three Ring System Compounds presented here were obtained according to general procedure shown below.

The mixture of anthracycline (0.1 mmol), 4-iodobutyraldehyde (200 μl) and diisopropylethylamine (100 μl, 0.6 mmol) in dimethylformamide (1 mL) was stirred at room temperature until disappearance of substrate. Progress of the reaction was monitored by thin-layer chromatography (TLC). Then, reaction mixture was diluted with dichloromethane (30 mL), washed with water, and dried over anhydrous sodium sulfate. The drying agent was filtered off, and solvent was evaporated to give a crude product which was then purified by column chromatography on silica gel using as an eluent chloroform.

Using this general procedure, the following specific compounds were made.

WP809, a Derivative of Daunorubicin

Compound WP809 (FIG. 3) was obtained according to general procedure, starting from daunorubicin hydrochloride.

$^1$HNMR (CDCl$_3$, δ): 13.89, 13.26 (2s, 1H ea, 6,11-OH), 7.99 (d, 1H, J$_{1,2}$-7.91 Hz, H-1), 7.74 (dd, 1H, J$_{1,2}$=J$_{2,3}$=8.15

Hz, H-2), 7.35 (d, 1H, J=8.4 Hz, H-3), 5.47 (dd, J=4.5 Hz, H-1'), 5.28 (bs, 1H, H-7), 511 (dd, 1H, J=5 Hz, J=1.2 Hz, H-1"), 4.79 (s, 1H, 9-OH), 4.06 (dq, 1H, $J_{5',6'}$=6.4 Hz, $J_{4',5'}$=2 Hz, H-5'), 4.04 (s, 3H, OMe), 3.83 (dd, 1H, $J_{3',4'}$=5.8 Hz, $J_{4',5'}$=1.8 Hz, H-4'), 3.27 (dd, 1H, $J_{3',2'a}$=13.4 Hz, $J_{3',4'}$=5.8 Hz, H-3'), 3.18 (dd, 1H, J=18.9 Hz, J=1.8 Hz, H-10), 3.07 (m, 1H, H-4"), 2.93 (d, 1H, J=18.9 Hz, H-10), 2.60-2.55 (m, 1H, H-4"), 2.40 (d, 1H, J=14.74 Hz, H-8), 2.38 (s, 3H, 14-CH$_3$), 2.03 (dd, J=14.7 Hz, J=3.2 Hz, H-8), 1.90–1.67 (m, 5H, H-2'a, 2'e, 2×3"), 2.01–2.00 (m, 1H, H-2"), 1.39 (d, 3H, $J_{5',6'}$=6.6 Hz, H-6").

WP836, a Doxorubicin Derivative

Compound WP836 (FIG. 4) was obtained according to general procedure, starting from doxorubicin hydrochloride.

$^1$HNMR (CDCl$_3$, δ); 13.92, 13.20 (2s, 1H ea, 6,11-OH), 8,05 (D, 1H, $J_{1,2}$=8.0 Hz H-1), 7.80 (dd, 1H, $J_{1,2}$=$J_{2,3}$=8.1 Hz, H-2), 7.41 (d, 1H, $J_{2,3}$=8.4 Hz, H-3), 5.52 (dd, 1H, $J_{1',2a}$=$J_{1',2e}$=4.7 Hz, H-1'), 5.35 (bs, 1H, H-7), 5.16 (d, 1H, J=4.2 Hz, H-1"), 4.93 (s, 1H, 9-OH), 4.78 (d, 2H, J=3.4 Hz, 14-CH$_2$), 4.10 (s, 3H, OMe), 4.04 (q, 1H, $J_{5',6'}$=6.5 Hz, H-5'), 3.91 (dd, 1H, $J_{3',4'}$=6 Hz, $J_{4',5'}$=1.5 Hz, H-4'), 3.32 (dd, 1H, $J_{3',2'a}$=12.86, $J_{3',4'}$=6.3 Hz, H-3'), 3.28 (d, 1H, J=20.6 Hz, H-10), 3.16–3.11 (m, 1H, H-4"), 2.67–2.61 (m, 1H, H-4"), 2.48 (d, 1H, J=14.7 Hz, H-8), 2.14 (dd,1H,J=14.7 Hz, J=3.9 Hz, H-8), 2.12–2.05 (m, 1H, H-2"), 1.97–1.70 (m, 5H, H-2'e, 2'a, 2×2", 2×3"), 1.38 (d, 1H, $J_{5',6'}$=6.4 Hz, H-6')

Anal. calcd. for C$_{31}$H$_{33}$N$_{11}$O×0.5 H$_2$O: C, 61.58; H, 5.67; N, 2.32. Found: C, 61.29; H, 5.54; N, 2.28.

Anal. calcd. for C$_{31}$H$_{33}$NO$_{10}$×0.5 H$_2$O: C, 63.26; H, 5.82; N, 2.38. Found: C, 63.23; H, 5.82; N, 2.33

WP846, a Derivative of 4'-Amino-3'-Hydroxy-Daunorubicin

Compound WP846 (FIG. 5) was obtained according to general procedure, starting from 4'-amino-3'-hydroxy-daunorubicin hydrochloride (WP608).

$^1$HNMR (CDCl$_3$, δ): 13.88, 13.30 (2s, 1H ea, 6,11-OH), 8.03 (d, 1H, $J_{1,2}$=7.91 Hz, H-1), 7.77 (dd, 1H, $J_{1,2}$=$J_{2,3}$=8.15 Hz, H-2), 7.38 (d, 1H, $J_{2,3}$=8.4 Hz, H-3), 5.49 (dd, 1H, $J_{1',2'e}$=7.0 Hz, $J_{1',2'a}$=6.1 Hz, H-1'), 5.30 (dd, 1H, J=3.7 Hz, J=2.1 Hz, H-7), 5.05 (dd, 1H, J=3.7 Hz, J=2.1 Hz, H-1"), 4.94 (s, 1H, 9-OH), 4.42 (ddd, 1H, $J_{3',4'}$=7.2 Hz, $J_{3',2'e}$=3.5 Hz, $J_{3',2'a}$=3.5 Hz, H-3'), 4.08 (s, 3H, OMe), 4.04 (dq, 1H, $J_{5',6'}$=6.2 Hz, $J_{5',4'}$=3 Hz, H-5'), 3,21 (dd, 1H, J=18.9 Hz, J=2 Hz, H-10), 3.15–3,12 (m, 1H, H-4"), 3.11 (dd, 1H, $J_{3',4'}$=7.2 Hz, $J_{4',5'}$=2.8 Hz, H-4'), 2.98 (d, 1H, J=18.9 Hz, H-10), 2.65–2.60 (m, 1H, H-4"), 2.53 (td, 1H, J=14.6 Hz, J=4.1 Hz, J=2 Hz, H-8), 2.42 (s, 3H, 14-CH$_3$), 2.36 (ddd, 1H, $J_{2'a,2'e}$15.2 Hz, $J_{2'a,1'}$=5.7 Hz, $J_{2'a,3}$=4.1 Hz, H-2'a), 2.03 (dd, 1H, J=14.7 (Hz, J=4.1 Hz, H-8), 2.08–2.03 (m, 1H, H-2"), 1.93–1.72 (m, 3H, H-2", 3"), 1.57 (ddd, 1H, $J_{2'a,2'e}$=15.2 Hz, $J_{2'e,1'}$=7.4 Hz, $J_{2'e,3'}$=3.1 Hz, H-2'e) 1.35 (d, 3H, $J_{5',6'}$=6.4 Hz, H-6').

WP851, a Derivative of 2'-Iodo-Daunorubicin

Compound WP851 (FIG. 6) was obtained according to general procedure, starting from 2'-iodo-daunorubicin (WP087).

$^1$HNMR (CDCl$_3$) δ: 13.90, 13.30 (2s, 1H ea, 6,11-OH), 8.04 (d, 1H, $J_{1,2}$=7.91 Hz, H-1), 7.77 (dd, 1H, $J_{1,2}$=$J_{2,3}$=8.15 Hz, H-2), 7.38 (d, 1H, $J_{2,3}$=8.4 Hz, H-3), 5.73 (d, 1H, $J_{1',2'}$=7.5 Hz, H-1'), 5.36 (dd, 1H, J=3.6 Hz, J=2.3 Hz, H-7), 5.24 (d, 1H, J=4.8 Hz, H-1"), 4.73 (s, 1H, 9-OH), 4.25 (dd, 1H, $J_{3',4'}$=7.9 Hz, $J_{4',5'}$=2.0 Hz, H-4'), 4.08 (s, 3H, OMe), 4.00 (dq, 1H, $J_{5',6'}$=6.4 Hz, $J_{4',5'}$=2.1 Hz, H-5'), 3.93 (dd, 1H, $J_{1',2'}$=7.5 Hz, $J_{2',3'}$=3.4 Hz, H-2'), 3.55 (dd, 1H, $J_{3',4'}$=8.0 Hz, $J_{2',3'}$=3.4 Hz, H-3'), 3.37–3,31 (m, 1H, H-4"), 3.23 (dd, 1H, J=18.9 Hz, J=1.8 Hz, H-10), 2.99 (d, 1H, J=18.9 Hz, H-10), 2.75–2.71 (m, 1H, H-4"), 2.45 (td, 1H, J=14.2 Hz, J=4.0 Hz, J=2.1 Hz, H-8), 2.40 (s, 3H, 14-Ch$_3$), 2.07 (dd, 1H, J=14.7 Hz, J=4.0 Hz, H-8), 2.02–1.96 (m, 1H, H-2"), 1.89–1.75 (m, 3H, H-2", 3"), 1.29 (d, 3H, $J_{5',6'}$=6.4 Hz, H-6').

WP840, a Derivative of 2'-Amino-3'-Hydroxy-Daunorubicin

Compound WP840 (FIG. 7) was obtained according to general procedure, starting from 2'-amino-3'-hydroxy-daunorubicin hydrochloride (WP842).

$^1$HNMR (CDCl$_3$, δ): 14.05, 13.31 (2s, 1H ea, 6,11-OH), 8,05 (d, 1H, $J_{1,2}$=7.91 Hz, H-1), 7.79 (dd, 1H, $J_{1,2}$=$J_{2,3}$=8.15 Hz, H-2), 7.40 (d, 1H, $J_{2,3}$=8.4 Hz, H-3), 5.49 (s, 1H, H-1'), 5.28 (bs, 1H, H-7), 5.06 (dd, 1H, J=3.4 Hz, J=3.4 Hz, H-1"), 4.43 (s, 1H, 9-OH), 4.12–4.08 (m, 1H, H-3'), 4.10 (s, 3H, OMe),3.79 (dq, 1H, $J_{5',6'}$=6.2 Hz, $J_{5',4'}$=8.7 Hz, H-5'), 3.60 (dd, 1H, $J_{3',4'}$=$J_{4',5'}$=8.7Hz, H-4'), 3.23 (dd, 1H, J=18.9 Hz, J=2 Hz, H-10), 3.03–2.97 (m, 1H, H-4")2.97 (d, 1H, J=18.9 Hz, H-10), 2.96 (d, 1H, $J_{2',3'}$=6.3 Hz, H-2'), 2.85–2.97 (m, 1H, H-4"), 2.42 (s, 3H, 14-CH$_3$), 2.38 (td, 1H, J=12.4 Hz, J=4.1 Hz, J=2.1 Hz, H-8), 2.22 (bs, 1H, 4'-OH), 2.12 (dd, 1H, J=14.7 Hz, J=4.4 Hz, H-8), 1.95–1.63 (m, 4H, H-3",2"), 1.38 (d, 3H, $J_{5',6'}$=6.1 Hz, H-6')

WP885, a Derivative of Idarubicin

Compound WP885 (FIG. 8) was obtained according to general procedure, starting from idarubicin. WP885 shows similar spectral characteristics to those of daunorubicin.

1-Ribo Analog of WP809

Figure 9:
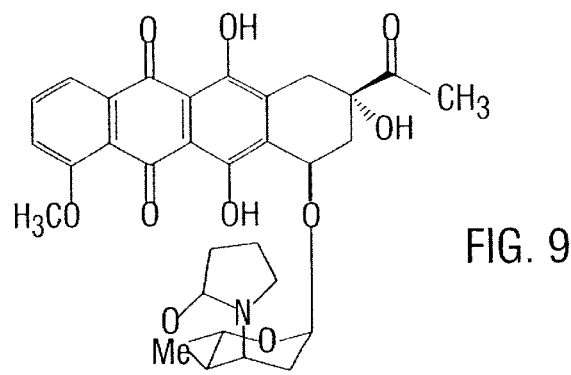
FIG. 9. 1-Ribo analog of WP 809
Figure 10A:
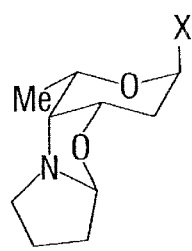
FIG. 10. Exemplary three ring systems ("x" denotes any suitable nucleic acid intercalating group or binding group that will bring the alkylating function of the three ring group into proximity with DNA, including, but not limited to, the anthracyclines disclosed herein).
Figure 10B:
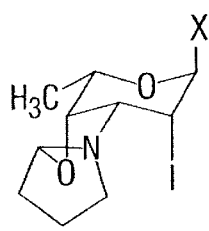
Figure 10C:
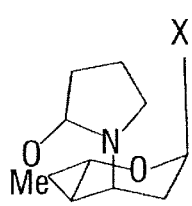
Figure 10D:
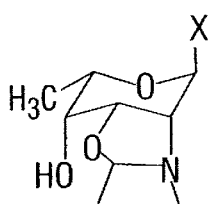
Figure 10E:
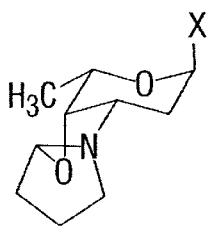

FIG. 9 shows a 1-ribo analog of WP809 which may be made according to the general procedures.

EXAMPLE 2

Design of DNA Alkylators

This example describes the design and evaluates new specific anthracycline-based DNA alkylators. In the design phase, the inventors envision that their synthetic efforts can be enhanced by molecular modeling based on existing structural data. In addition to 3-base pair binding anthracyclines, which will serve as templates on which the inventors can build alkylating moieties, the inventors will use a new class of bisintercalating anthracyclines that show greater sequence specificity than other class of anthracyclines. The dependence of the cross-linking process on formaldehyde can be reduced by incorporating into the new anthracyclines various moieties that are able to form covalent cross-links. The potential of mitoxantrone as a template for mitoxantrone-based alkylators will also be tested. Thus, optimal DNA binding and cross-linking anthracyclines can be identified and the significance of differences in specificity with respect to their therapeutic potential can be investigated.

Design of DNA Alkylators by Cross-linking Experiments and Molecular Modeling

The inventors have demonstrated that it is possible to cross-link DNR with DNA via a methylene bridge between the 3'-amine of anthracyclines and the N2 of guanine in a formaldehyde-mediated reaction. Herein, the inventors contemplate the design of novel DNA alkylators that imitate the mechanism and stereochemical requirements of formaldehyde-mediated cross-linking, and the use of molecular modeling to follow formaldehyde-mediated cross-linking.

The rationale for the design of base-specific sequence-selective alkylators of DNA is based on a model of formaldehyde-mediated cross-linking of DNR with DNA and the analysis of its mechanism. In designing new alkylators, one should focus on three elements: (1) the proximity of the reacting centers, (2) the mechanism of the formation of a covalent bond, and (3) the sequence selectivity and base specificity of alkylation. For the specific sequences, the proximity of reacting atoms of drug and DNA can be assessed using molecular modeling; for DNA, the proximity can be checked experimentally by examining the formaldehyde-mediated cross-linking of the drug to DNA.

Methods

Drug-DNA cross-linking reactions and the reaction of alkylators with DNA can be studied as follows. First, using herring sperm DNA, it is possible to study (1) the ability of compounds to form cross-links with DNA in a formaldehyde-mediated reaction and (2) the ability of alkylators to form spontaneous cross-links with DNA. One can initiate cross-linking reactions using a method described in Leng et al., 1996. One could react 350 $\mu$M DNA (bp) with 35 $\mu$M of the drug (with or without formaldehyde) in buffered solution at 24° C. Reaction can be stopped by addition of SDS to a final concentration of 1.33% or by phenol extraction with buffer-saturated phenol. The amount of the drug covalently bound can be estimated by determining the difference between the initial drug concentration and the amount of the drug extracted.

Formaldehyde-mediated cross-linking reactions of DNR and DNA provided the inventors information about the distances between reactive centers on the DNA template and on the bound drug and with information about the stereochemical requirements for cross-linking. Therefore, it is possible to design novel and more stable cross-linking moieties at the C-3' position and examine their effectiveness in the DNA template-catalyzed reaction with the N2 amine of guanine.

The mechanism by which formaldehyde is able to cross-link DNA with drug is based on formation of reactive iminium ions. Iminium ions are expected to be intermediates formed by, and responsible in part for the activity of, drugs like cyanomorpholino-DOX (MRA-CN), morpholino-DOX, N-(5,5-diacetoxy-pentyl)-DOX, and barminomycin. All of these drugs should be able to form covalent links with DNA. However, there are anthracyclines whose alkylating moieties are mechanistically different from the iminium ion-alkylating moiety that have been studied for their DNA binding and for their clinical potential.

Unlike previous approaches to designing the alkylating moiety at C-3' in anthracyclines, the approach the inventors propose to use is different. In brief, the inventors propose to remove the amino group from the C-3' position. The inventors contemplate that, while the presence of the amino group is essential to forming iminium ion-reactive intermediates, it may not be essential for forming other types of alkylating moieties. So far the inventors have designed three different types of alkylating moieties that all share one common trait: their reactive sites are the same distance from the C-3' as the iminium carbon WP809.

Figures 11A, 11B:
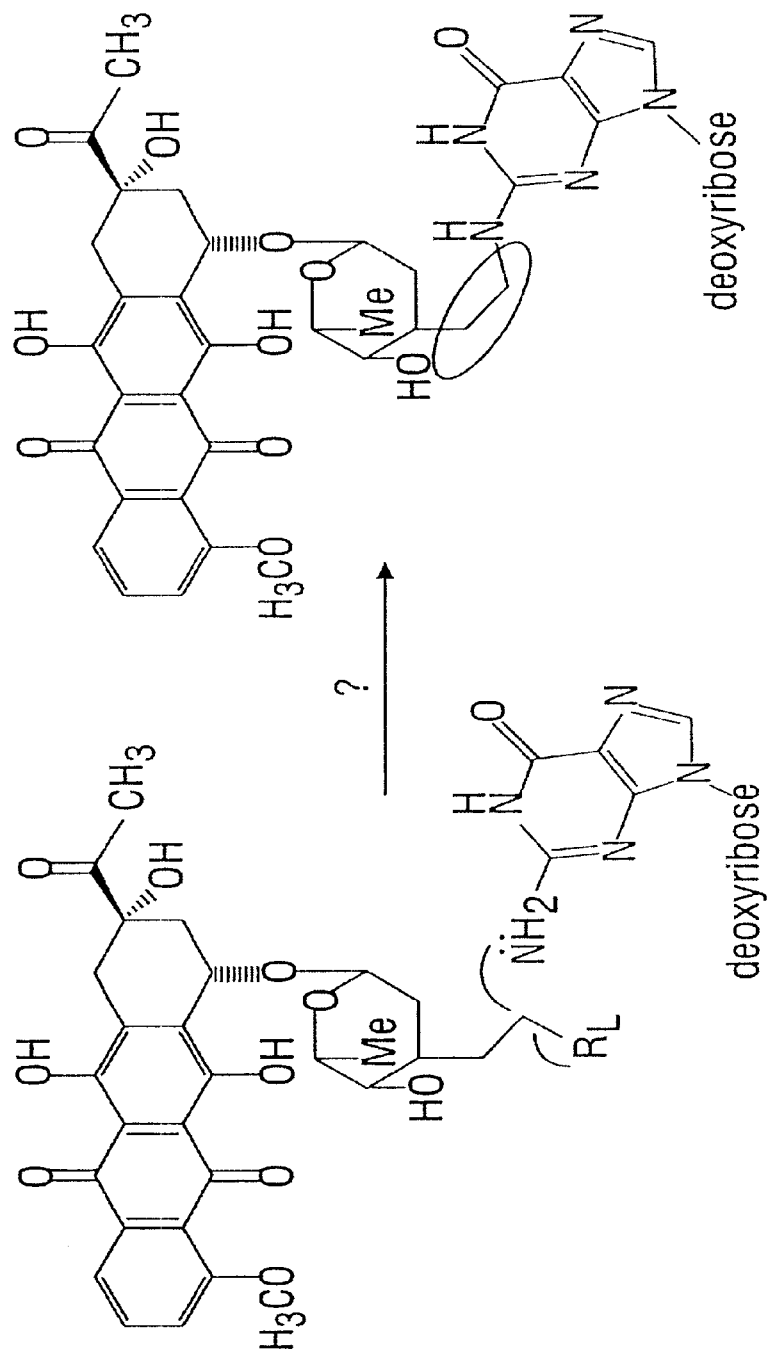
FIG. 11. Synthesis of some compounds of the present invention.
Figures 11C, 11D:
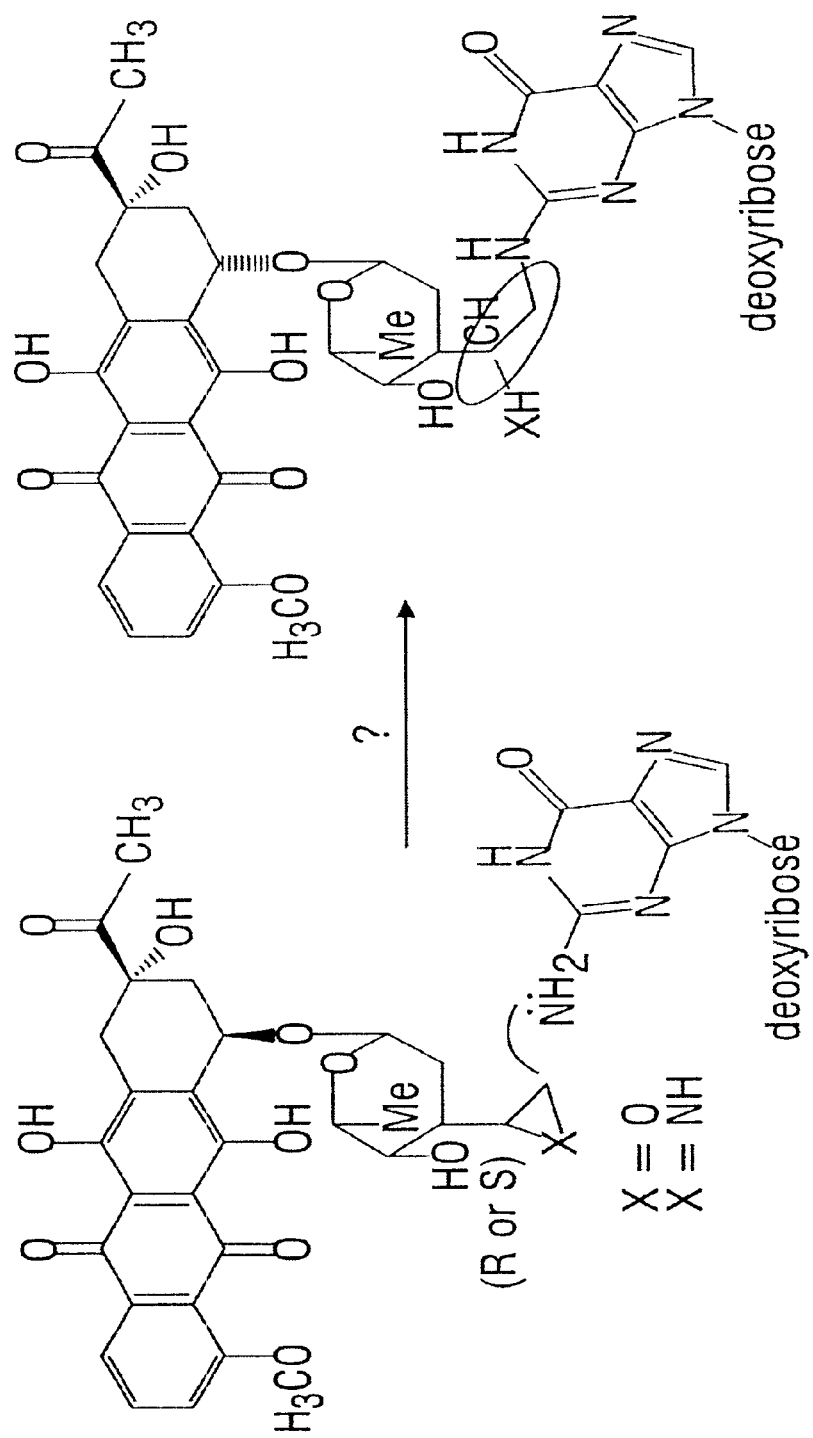
Figure 14:
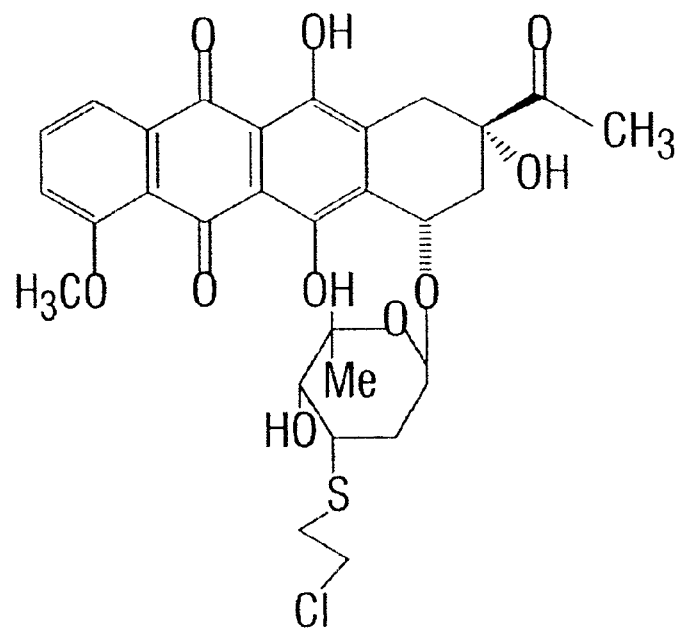
FIG. 14. A 3'-thiol, L-lyxo anthracycline.
Figure 15:
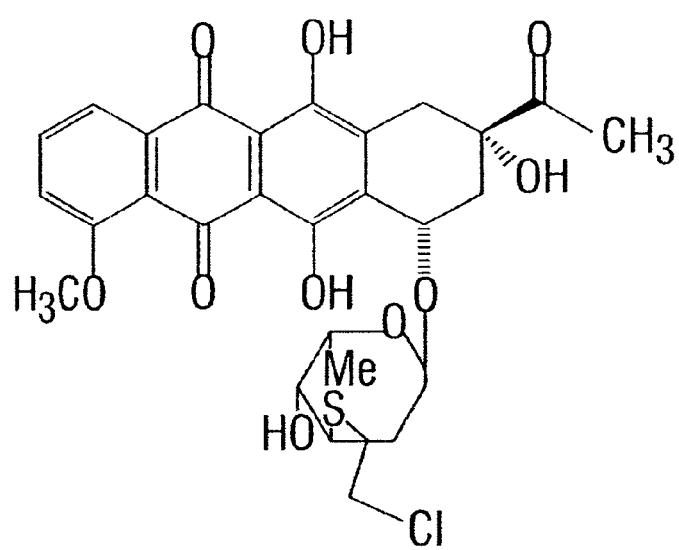
FIG. 15. A 3'-thiol, L-xylo anthracycline.

The scheme for preparing some compounds is described in FIG. 11. To create the analog of FIG. 12, one may add at C-3' an ethyl chain that has an easy leaving group like mesyl, tosyl, or iodine at terminal position. Alternatively, if such a group is not reactive enough, one can introduce a triflate-type leaving group. In the analogs of FIG. 13, the alkyl chain carries an epoxide or aziridine function which can be opened by nucleophilic $S_N2$ attack or acid catalyzed $S_N1$ reaction. In the analogs of FIGS. 14 and 15, one will incorporate into previously prepared 3'-mercapto DNR and DOX a simple alkylating moiety, i.e., a chloroethly chain. The preparation of both configurational isomers at C-3', i.e., the L-lyxo (FIG. 14) and L-xylo (FIG. 15) configurations is contemplated.

The proposed compounds should provide a selection of novel and more stable cross-linking moieties that can form a covalent bond with 2N amine of guanine. The cytotoxicity of the proposed analogs can be routinely assessed as described below. The stability of the drugs created will also be tested by standard techniques known to one of skill in the art.

EXAMPLE 3

Assessment of Antitumor Activity In Vitro

Compounds synthesized using the methods described above were tested using a standard MTT assay (Green et al., 1984) against human carcinoma sensitive (KB) and multi-drug-resistant (KBV1) cells and MCF-7 and MCF-7/VP-16 resistant cells characterized as having the MRP (multi-drug resistant associated protein) phenotype. The use of an MTT assay using these cells is recognized as an accepted assay for anti-tumor activity by those in the field.

Methods

In vitro Cytotoxicity against MCF-7, MCF-7/VP-16, and MCF-7/DOX cell lines. In vitro drug cytotoxicities against human breast carcinoma wild-type MCF-7 and MRP-resistant MCF-7/VP-16 cells were assessed by using the MTT reduction assay, as previously reported (Green et al., 1984). The MTT dye was obtained from Sigma Chemical Co. (St. Louis, Mo.). Cells were plated in 96-well microassay culture plates ($10^4$ cells/well) and grown overnight at 37° C. in a 5% $CO_2$ incubator. Drugs were then added to the wells to achieve a final drug concentration ranging from 0.1 to 50 $\mu$g/mL. Four wells were used for each concentration. Control wells were prepared by adding appropriate volumes of calcium- and magnesium-free PBS (pH 7.4). Wells containing culture medium without cells were used as blanks. The plates were incubated at 37° C. in a 5% $CO_2$ incubator for 72 hours. Upon completion of the incubation, 20 $\mu$L of stock MTT dye solution (5 mg/mL) was added to each well. After a 4-hour incubation, 100 $\mu$L of buffer containing 50% N,N-dimethylformamide and 20% SDS was added to solubilize the MTT formazan. Complete solubilization was achieved by placing the plate in a mechanical shaker for 30 minutes at room temperature. The optical density of each well was then measured with a microplate spectrophotometer at a wavelength of 570 nm. The percent cell viability was calculated by the following equation:

% cell viability=(OD treated wells/OD control wells)×100 where OD is the mean optical density from four determinations. The percent cell viability values were plotted against the drug concentrations used, and the $ID_{50}$ was calculated from the curve. Cytotoxicity experiments were repeated at least three times.

Results and Discussion

Drug resistance, both de novo and acquired, by human tumors is currently a major factor limiting the effectiveness of chemotherapy. Thus, for the in vitro evaluation of substituted anthracyclines having a three ring system, the inventors selected two sensitive cell lines: a human carcinoma KB and MCF-7 human breast cancer, the multi-drug-resistant (MDR) counterpart of KB (KBV1 carcinoma), which overexpresses MDR1 gene that encodes a membrane transport glycoprotein (P-gp), the MCF-7/VP-16 cell line that overexpresses the multi-drug-resistant associated protein (MRP), and the MCF-7/dox cell line which overexpresses MDR1 gene. Using this system, the inventors evaluate a drug's cytotoxic potential against human tumors and at the same time identify compounds that might have unique activity against MDR tumors (Priebe et al., 1993).

Table 2 shows the in vitro evaluation of cytotoxic properties of WP809 and WP836, doxorubicin (DOX), and daunorubicin (DNR) in the above-described cells.

TABLE 2

IN VITRO CYTOTOXICITY OF AGAINST SENSITIVE AND TYPICAL MDR AND MRP TUMOR CELL LINES[1]

|  | KB ng/mL | KBV1 ng/mL | RI[2] | MCF-7 ng/mL | MCF-7/VP-16 ng/mL | RI[3] | MCF-7/dox ng/mL | RI[4] |
|---|---|---|---|---|---|---|---|---|
| Experiment 1 | | | | | | | | |
| WP809 | 5.3 ± 2.34 | 6.7 ± 1.69 | 1.3 | | | | | |
| WP836 | 0.65 ± 0.14 | 2.76 ± 2.15 | 4.2 | 0.43 ± 0.06 | 0.43 ± 0.06 | 1 | 0.67 ± 0.15 | 1.56 |
| DOX | 340 ± 100 | >100,000 | >294 | 300 ± 170 | 2,860 ± 1,610 | 9.53 | 100,000 | >333 |
| DNR | 220 ± 10 | 10,000 ± 0 | 45 | | | | | |
| Experiment 2 | | | | | | | | |
| WP809 | 5.7 ± 1.9 | 8.1 ± 1.4 | 1.42 | 4.00 ± 0.00 | 4.16 ± 0.28 | 1.04 | 6.67 ± 2.08 | 1.67 |
| WP836 | 0.5 ± 0.06 | 0.7 ± 0.06 | 1.4 | | | | | |
| DOX | | | | 240 ± 50 | 860 ± 160 | 3.58 | >100,000 | >416 |

Direct comparisons of the cytotoxicity of WP809 and WP836 with DOX and DNR indicated that the three ring system increases drastically the potency of those compounds. Doxorubicin analog WP836 is more potent that daunorubicin analog WP809 by several fold. However, both compounds show extreme increases in cytotoxicity over doxorubicin and daunorubicin in regard to MDR lines. This suggests that the cytotoxicity of WP809 and WP836 is not linked to the presence of membrane transporters.

EXAMPLE 4

Treatment of Tumors with Substituted Anthracyclines Having a Three Ring System

Treatment with the substituted anthracyclines having a three ring system and their respective free amines of the present invention is similar to the treatment regimes of other anthracyclines and their derivatives, although some modifications to dosage may be warranted For example, standard treatment with doxorubicin is described in *Remington's Pharmaceutical Sciences* as follows.

Doxorubicin is administered intravenously to adults at 60 to 75 mg/m$^2$ at 21-day intervals or 25 to 30 mg/m$^2$ on each of 2 or 3 successive days repeated at 3- or 4-week intervals or 20 mg/m$^2$ once a week. The lowest dose should be used in elderly patients, when there is prior chemotherapy or neoplastic marrow invasion or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in patients with abnormal heart function and 400 mg/m$^2$ on each of 3 consecutive days, repeated every 4 weeks. Prescribing limits are as with adults. It has been reported that a 96-hour continuous infusion is as effective as and much less toxic than the same dose given by golus injections.

Of course, modifications of the treatment regimes due to the unique nature of the substituted anthracyclines having a three ring system of the present invention are possible and well within the ability of one skilled in the art. Appropriate modifications may be ascertained by following the protocols in the following examples for in vivo testing and developments of human protocols.

EXAMPLE 5

In Vivo Prevention of Tumor Development Using Substituted Anthracyclines Having a Three Ring System In an initial round of in vivo trials, a mouse model of human cancer with the histologic features and metastatic potential resembling tumors seen in humans (Katsumata et al., 1995) is used. The animals are treated with substituted anthracyclines having a three ring system of the present invention to determine the suppression of tumor development.

Substituted anthracyclines having a three ring system are tested in vivo for antitumor activity against murine leukemia L1210, P388, and P388 resistant to doxorubicin. In conjunction with these studies, the acute and sub-acute toxicity is studied in mice (LD10, LD50, LD90). In a more advanced phase of testing, the antitumor activity of substituted anthracyclines having a three ring system against human xenografts is assessed and cardiotoxicity studies performed is done in a rat or rabbit model.

These studies are based on the discovery that substituted anthracyclines having a three ring system of the current invention have anti-cancer activity for MDR cancer cells. The current example uses of substituted anthracyclines having a three ring system, to provide a useful preventive and therapeutic regimen for patients with MDR tumors.

Two groups of mice of a suitable cancer model are treated with doses of substituted anthracyclines having a three ring system. Several combinations and concentrations of substituted anthracyclines having a three ring system are tested. Control mice are treated with buffer only.

The effect of substituted anthracyclines having a three ring system on the development of breast tumors is compared with the control group by examination of tumor size and histopathologic examination (breast tissue is cut and stained with hematoxylin and eosin) of breast tissue. With the chemopreventive potential of WP 715, WP 722 and other substituted anthracyclines having a three ring system of the present invention, it is predicted that, unlike the control group of mice that develop tumors, the testing group of mice is resistant to tumor development.

EXAMPLE 6

Human Treatment with Substituted Anthracyclines Having a Three Ring System

This example describes a protocol to facilitate the treatment of cancer using substituted anthracyclines having a three ring system.

A cancer patient presenting, for example, an MDR cancer is treated using the following protocol. Patients may, but need not, have received previous chemo- radio- or gene therapeutic treatments. Optimally, the patient exhibits adequate bone marrow function (defined as peripheral absolute granulocyte count of >2,000/mm3 and platelet count of 100, 000/mm3, adequate liver function (bilirubin 1.5 mg/dl) and adequate renal function (creatinine 1.5 mg/dl)).

Exemplary Protocol for the Treatment of Multi-Drug Resistant Cancer

A composition of the present invention is typically administered orally or parenterally in dosage unit formulations containing standard, well known, non-toxic physiologically acceptable carriers, adjuvants, and vehicles as desired. The term parenteral as used herein includes subcutaneous injections, intravenous, intramuscular, intra-arterial injection, or infusion techniques. The substituted anthracyclines having a three ring system may be delivered to the patient before, after, or concurrently with the other anti-cancer agents.

A typical treatment course may comprise about six doses delivered over a 7- to 21-day period. Upon election by the clinician, the regimen may be continued six doses every three weeks or on a less frequent (monthly, bimonthly, quarterly etc.) basis. Of course, these are only exemplary times for treatment, and the skilled practitioner will readily recognize that many other time-courses are possible.

A major challenge in clinical oncology is that many cancers are multi-drug resistant. One goal of the inventors' efforts has been to find ways to improve the efficacy of chemotherapy. In the context of the present invention, the substituted anthracyclines having a three ring system that have a surprising activity against such cancers.

To kill MDR cancer cells using the methods and compositions described in the present invention, one will generally contact a target cell with a bisanthracycline of the present invention. These compositions are provided in an amount effective to kill or inhibit the proliferation of the cell.

In certain embodiments, it is contemplated that one would contact the cell with agent(s) of the present invention about every 6 hours to about every one week. In some situations, however, it may be desirable to extend the time period for treatment significantly where several days (2, 3, 4, 5, 6, 7 or more) to several weeks (1, 2, 3, 4, 5, 6, 7, or more) lapse between respective administrations.

Regional delivery of substituted anthracyclines having a three ring system is an efficient method for delivering a therapeutically effective dose to counteract the clinical disease. Likewise, the chemotherapy may be directed to a particular affected region. Alternatively, systemic delivery of active agents may be appropriate.

The therapeutic composition of the present invention is administered to the patient directly at the site of the tumor. This is in essence a topical treatment of the surface of the cancer. The volume of the composition should usually be sufficient to ensure that the tumor is contacted by the substituted anthracyclines having a three ring system.

In one embodiment, administration simply entails injection of the therapeutic composition into the tumor. In another embodiment, a catheter is inserted into the site of the tumor, and the cavity may be continuously perfused for a desired period of time.

Clinical responses may be defined by acceptable measure. For example, a complete response may be defined by the disappearance of all measurable disease for at least a month, whereas a partial response may be defined by a 50% or greater reduction of the sum of the products of perpendicular diameters of all evaluable tumor nodules or at least one month with no tumor sites showing enlargement. Similarly, a mixed response may be defined by a reduction of the product of perpendicular diameters of all measurable lesions by 50% or greater, with progression in one or more sites.

Of course, the above-described treatment regimes may be altered in accordance with the knowledge gained from clinical trials such as those described in Example VI. Those of skill in the art are able to take the information disclosed in this specification and optimize treatment regimes based on the clinical trials described in the specification.

EXAMPLE 7

Clinical Trials of the Use of Substituted Anthracyclines Having a Three Ring System in Treating Multi-Drug Resistant Cancer This example is concerned with the development of human treatment protocols using the substituted anthracyclines having a three ring system. These compounds are of use in the clinical treatment of various MDR cancers in which transformed or cancerous cells play a role. Such treatment is a particularly useful tool in anti-tumor therapy, for example, in treating patients with ovarian, breast and lung cancers that are resistant to conventional chemotherapeutic regimens.

The various elements of conducting a clinical trial, including patient treatment and monitoring, is known to those of skill in the art in light of the present disclosure. The following information is being presented as a general guideline for use in establishing substituted anthracyclines having a three ring system drugs made by the use of this invention, in clinical trials.

Patients with human metastatic breast and/or epithelial ovarian carcinoma, colon cancer leukemia, or sarcoma are chosen for clinical study. Measurable disease is not required, however the patient must have easily accessible pleural effusion and/or ascites. Further the patients must carry tumors that express MDR phenotype. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.

In regard to the substituted anthracyclines having a three ring system drug administration, a Tenckhoff catheter, or alternative device, may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, p185) and in the cells (E1A, p185) may be assessed and recorded.

In the same procedure, substituted anthracyclines having a three ring system may be administered. The administration may be in the pleural/peritoneal cavity, directly into the tumor, or in a systemic manner. The starting dose may be 0.5 mg/kg body weight. Three patients may be treated at each dose level in the absence of grade >3 toxicity. Dose escalation may be done by 100% increments (0.5 mg, 1 mg, 2 mg, 4 mg) until drug related Grade II toxicity is detected. Thereafter, dose escalation may proceed by 25% increments. The administered dose may be fractionated equally into two infusions, separated by 6 hours if the combined endotoxin levels determined for the lot of bisanthracycline exceed 5 EU/kg for any given patient.

The substituted anthracyclines having a three ring system may be administered over a short infusion time or at a steady rate of infusion over a 7- to 21-day period. The bisanthracycline infusion may be administered alone or in combination with the anti-cancer drug. The infusion given at any dose level is dependent upon the toxicity achieved after each. Hence, if Grade II toxicity was reached after any single infusion, or at a particular period of time for a steady rate infusion, further doses should be withheld or the steady rate infusion stopped unless toxicity improves. Increasing doses of substituted anthracyclines having a three ring system in combination with an anti-cancer drug is administered to groups of patients until approximately 60% of patients show unacceptable Grade III or IV toxicity in any category. Doses that are ⅔ of this value could be defined as the safe dose.

Physical examination, tumor measurements, and laboratory tests should, of course, be performed before treatment and at intervals of about 3–4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored, e.g. CEA, CA 15-3, p185 for breast cancer, and CA 125, p185 for ovarian cancer.

To monitor disease course and evaluate the anti-tumor responses, it is contemplated that the patients should be examined for appropriate tumor markers every 4 weeks, if initially abnormal, with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12-100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15-3, CA 125, p185) and in the cells (p185) may be assessed. For an example of an evaluation profile, see Table 3. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. A urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least one month with no tumor sites showing enlargement. Similarly, a mixed response may be defined by a reduction of the product of perpendicular diameters of all measurable lesions by 50% or greater with progression in one or more sites.

TABLE 3

EVALUATIONS BEFORE AND DURING THERAPY

| EVALUATIONS | PRE-STUDY | TWICE WEEKLY | WEEKLY | EVERY 4 WEEKS | EVERY 8 WEEKS |
|---|---|---|---|---|---|
| History | X | | | X | |
| Physical | X | | | X | |
| Tumor Measurements | X | | | X | |
| CBC | X | $X^1$ | X | | |
| Differential | X | $X^1$ | X | | |
| Platelet Count | X | X˙ | X | | |
| SMA12-100 (SGPT,Alkaline Phosphatase,bilirubin, Alb/Total Protein) | X | | X | | |
| Coagulation Profile | X | | | X | |
| Serum Tumor markers (CEA, CA15-3, CA-125, Her-2/neu) | X | | | $X^3$ | |
| Urinalysis | X | | | X | |
| X-rays: | | | | | |
| chest | X | | $X^4$ | | |
| others | X | | | | X |
| Pleural/Peritoneal Fluids: (cellularity, cytology, LDH, tumor markers, E1A, HER-2/neu) | X | | $X^5$ | X | |
| Spirometry and DLCO | X | | | $X^6$ | $X^6$ |

[1]For the first 4 weeks, then weekly, if no myelosuppression is observed.
[2]As indicated by the patient's condition.
[3]Repeated every 4 weeks if initially abnormal.
[4]For patients with pleural effusion, chest X-rays may be performed at 72 hours after first dose, then prior to each treatment administration.
[5]Fluids may be assessed 72 hours after the first dose, weekly for the first two courses and then every 4 weeks thereafter.
[6]Four and eight weeks after initiation of therapy.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Arcamone F., Doxorubicin. Anti-Cancer Antibiotics. New York: Academic Press, 1981.

Bell et al., *J. Clin. Oncol.*, 3:311, 1985

Bertino, *J. Clin. Oncol.*, 3:293, 1985

Bodley, et al., *Cancer Res.*, 49:5969–5978, 1989.

Bodley et al., *Cancer Res.*, 49:5969.

Booser D J and Hortobagyi G N., "Anthracycline Antibiotics in Cancer Therapy. Focus on Drug Resistance", Drugs, 47:223–258, 1994.

Bradley et al., *Biochem. Biophys. Acta.*, 948:87, 1988.

Capranico et al., "Sequence-Selective Topoisomerase II Inhibition by Anthracycline Derivatives in SV40 DNA: Relationship with DNA Binding Affinity and Cytotoxicity", *Biochem*, 29:562–569, 1990.

Chaires et al., "Structure-Based Design of a New Bisintercalating Anthracycline Antibiotic," *J. Med. Chem.*, 35:2047–2053, 1997.

Curt et al., *Cancer Treat. Rep.*, 68:87, 1984.

Danks et al., *Cancer Res.*, 47:1297, 1987.

Denny et al., "Potential Anti-tumor Agents. 39. Anilino Ring Geometry of Amsacrine and Derivatives: Relationship to DNA binding and Anti-tumor Activity", *J. Med. Chem.*, 26(11): 1625–1630, 1983.

Dervan P. *Science*, 232:464–471, 1986.

Fojo et al., *P.N.A.S.*, 84:265, 1987.

Ganapath, et al., *Br. J. Cancer*, 60:819, 1989.

Gao et al., "Substitution at C-2' of daunosamine in the anticancer drug daunorubicin alter its DNA-binding sequence specificity," *Eur. J. Biochem.*, 240:331–335, 1996.

Goldie et al., *Cancer Res.*, 44:3643, 1984.

Goldie et al., *Cancer Treat. Rep.*, 63:1727, 1979.

Green et al., *J. Immunol. Methods*, 70:257–268, 1984.

Gros et al., *Nature*, 323:728, 1986

Hu et al., "Structure of a DNA-Bisdaunomycin Complex," Biochemistry, 36:5940–5946, 1997.

Israel et al., 1987.

Israel et al., *Cancer Chemother. Pharmacol.*, 25:177, 1989.

Katsumata et al., "Prevention of Breast Tumor Development In Vivo by Down-Regulation of the p 185$^{neu}$ Receptor", *Nature Med.*, 1:644–648, 1995.

Kolate, *Science*, 231:220, 1986.

Leng et al., "Base Specific and Regioselective Chemical Cross-linking of Daunorubicin to DNA," *J. Am. Chem. Soc.*, 118:4731–4738, 1996.

Lown J W, "Targeting the DNA Minor Groove for Control of Biological Function: Progress, Challenges and Prospects", *Chemtracts—Org. Chem.*, 6:205–237, 1903.

Lown J W, "Anthracycline and Anthracenedione-Based Anticancer Agents, Bioactive Molecules, Vol. 6, Amsterdam: Elsevier, 1988.

Marchini et al., "Sequence-specific DNA interactions by novel alkylating anthracycline derivatives," *Anti-Cancer Drug Design*, 10:641–653, 1995.

Norris et al., "Expression of the gene for multidrug-resistance-associated protein and outcome in patients with neuroblastoma", *N. Engl. J. Med*, 334:231–238, 1996.

Nowell, *Cancer Res.*, 46:2203, 1986.

Pommier et al., *Cancer Res*.

Priebe et al., "3'-Hydroxy-esorubicin substituted at C-2'", *J. Antibiot*, 45:386–393, 1992.

Priebe et al., "Removal of the basic center from doxorubicin partially overcomes multidrug resistance and decreases cardiotoxicity", *Anti-Cancer Drugs*, 4:37–48, 1993.

Priebe W, "Anthracycline Antibiotics. Novel Analogues, Methods of Delivery, and Mechanisms of Action", Washington, DC: American Chemical Society, 1995.

Priebe W. "Mechanism of Action-Governed Design of Anthracycline Antibiotics: A "Turn-Off/Turn-On" Approach", *Current Pharmaceutical Design*, 1:51–68, 1995.

Robinson et al., "Binding of Two Novel Bisdaunorubicins to DNA Studies by NMR Spectroscopy," *Biochemistry*, 36:8663–8670, 1997.

Rubinstein et al., "Comparison of In Vitro Anti-Cancer-Drug-Screening Data Generated with A Tetrazolium Assay Versus a Protein Assay Against a Diverse Panel of Human Tumor Cell Lines", *J. Nat'l. Cancer Inst.*, 82:1113–1120, 1990.

Stryer, "Biochemistry", Freeman and Co., 1981.

Sweatman et al, *J. Cell. Pharmacol.*, 1:95–102.

Traganos et al., *Cancer Res.*, 45:6273, 1985.

Wakelin LPG, "Medicinal Research Rev.", 6:275–340, 1986.

Young et al., *N. Engl. J. Med.*, 312:692, 1985.

U.S. Pat. No. 4,263,428 Apr. 21, 1981.

U.S. Pat. No. 4,345,070, Aug. 17, 1982.

U.S. Pat. No. 4,438,105, Mar. 20, 1984.

What is claimed is:

1. A substituted anthracycline having the formula:

wherein $R^1$ is a hydroxyl group (—OH), a methoxy group (—OCH$_3$), an alkoxy group having 1–20 carbon atoms, an alkyl group having 1–20 carbon atoms, an aryl group having 6–20 carbon atoms, a fatty acyl group having the structure —O—CO(CH2)$_n$CH$_3$, wherein n=an integer from 1 to about 20, or a fatty acyl group having the structure —O—CO(CH2)$_l$(CH═CH)$_m$(CH2)$_n$CH$_3$, wherein l is an integer between 1 to 3, m is an integer between 1 and about 6, and n is an integer between 1 to about 9;

each of $R^2$ and $R^3$ is, independently of the other, a hydrogen (—H) group, a hydroxyl group (—OH), a methoxy group (—OCH$_3$) or a double bonded oxygen moiety;

$R^4$ is a hydrogen (—H) group, a hydroxyl group (—OH), a methoxy group (—OCH$_3$) or a halide;

each of $Y^1$ and $Y^2$ is, independently of the other, a hydrogen (—H) group; a hydroxyl group (—OH); a methoxy group (—OCH$_3$); or a double bonded oxygen, sulphur, or nitrogen group;

$R^5$–$R^{12}$ are, independently, —H, —OH, a halide, —$OR^{13}$, —SH, —$SR^{13}$, —$NH_2$, —$NHR^{13}$, —$N(R^{13})_2$; $R^5$–$R^{12}$ can additionally independently be a saccharide; or $R^9$ can additionally be $CH_3$, with the proviso that:

both of $R^6$ and $R^7$ or both of $R^5$ and $R^8$ or both of $R^5$ and $R^{11}$ or both of $R^6$ and $R^{12}$ are involved in forming a three ring structure; wherein said three ring structure contains three heteroatoms selected from the group consisting of O and N and the rings of said three ring structure have 5 or 6 members; or either of $R^5$ and $R^6$ is independently a mercapto-haloalkyl group; an ether alkyl group containing an easy leaving group; an alkyl group containing an easy leaving group or an ether alkyl group containing an aziridine, oxirane, thiirane, oxetane or thietane ring; and $R^{13}$ is a methyl group, an alkoxy group having 1–20 carbon atoms, an alkyl group having 1–20 carbon atoms, an aryl group having 6–20 carbon atoms, a fatty acyl group having the structure —$CO(CH_2)_nCH_3$, wherein n=an integer from 1 to about 20, or a fatty acyl group having the structure —$CO(CH2)_l(CH=CH)_m(CH2)_nCH3$, wherein l is an integer between 1 to 3, m is an integer between 1 and about 6, and n is an integer between 1 to about 9.

2. The compound of claim 1 having the formula:

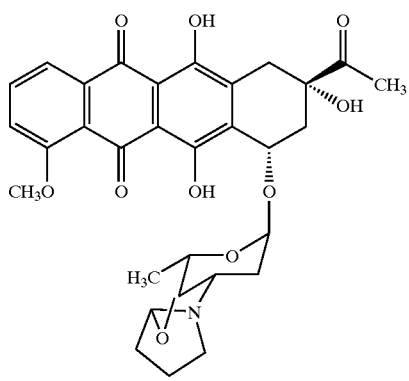

3. The compound of claim 1 having the formula:

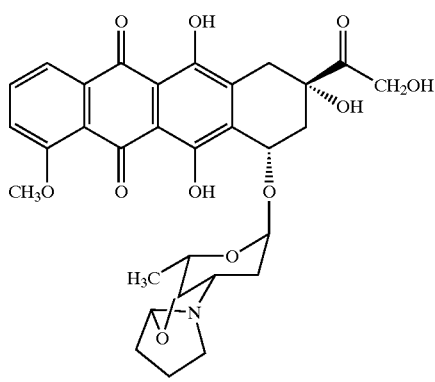

4. The compound of claim 1 having the formula:

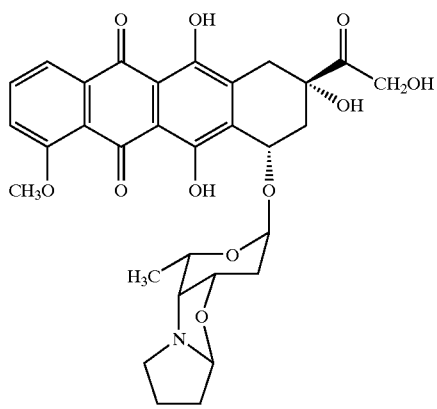

5. The compound of claim 1 having the formula:

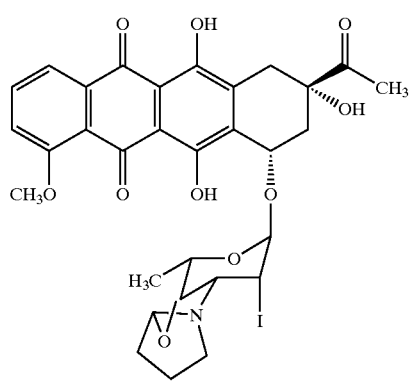

6. The compound of claim 1 having the formula:

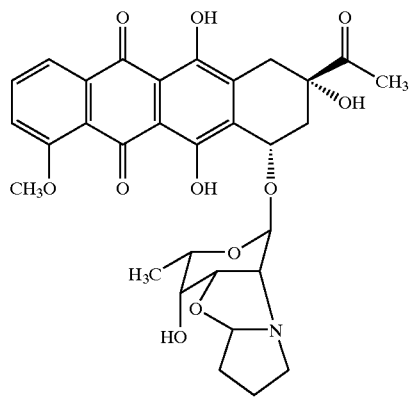

7. The compound of claim 1 having the formula:
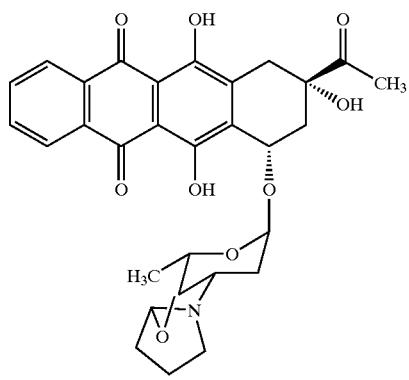
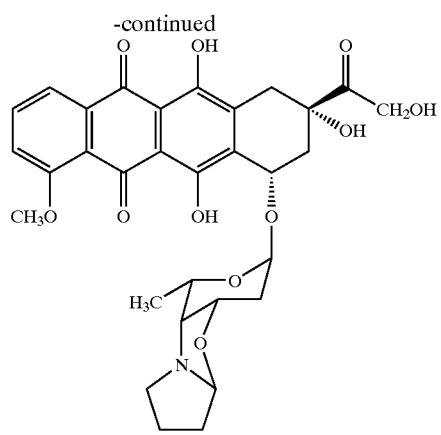
8. The compound of claim 1 having the formula:
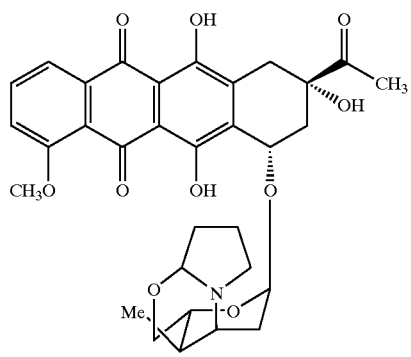
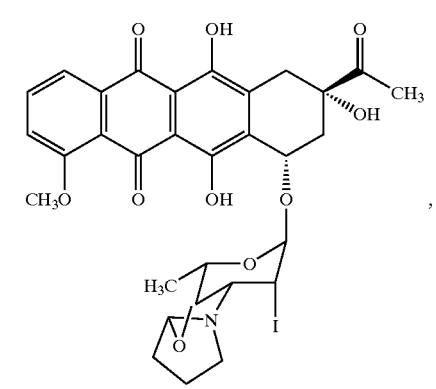
9. The compound of claim 1, further defined as having one of the formulae:
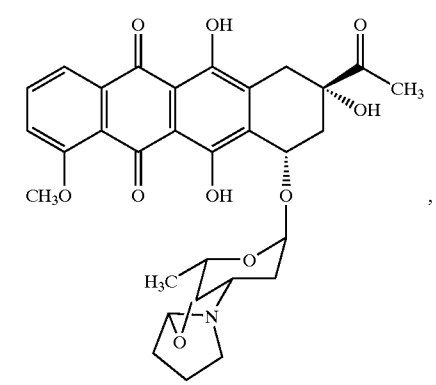
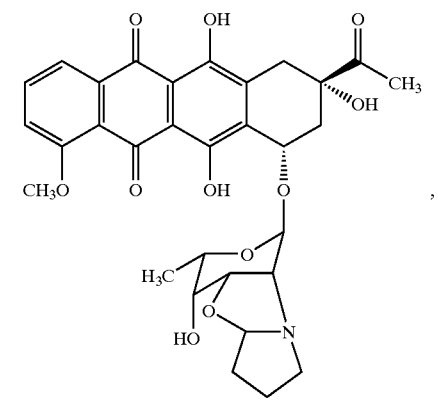
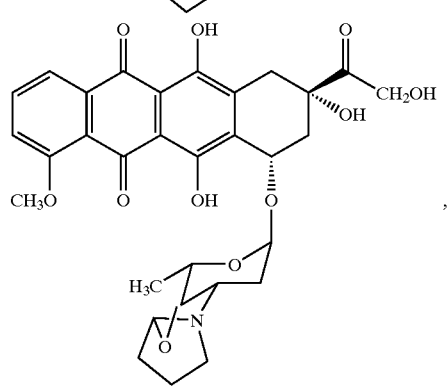
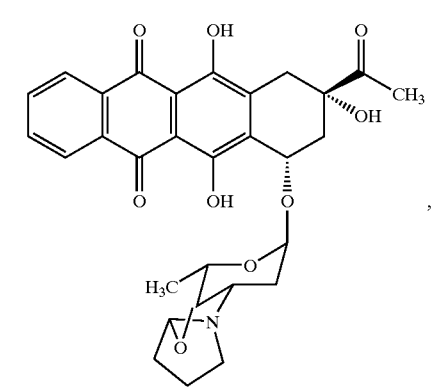

-continued
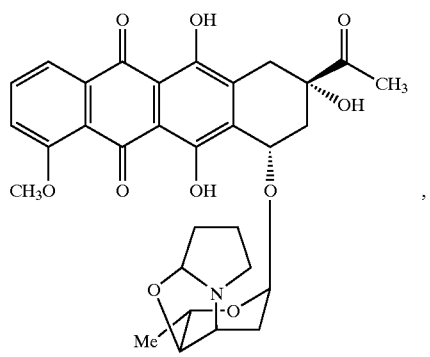
,
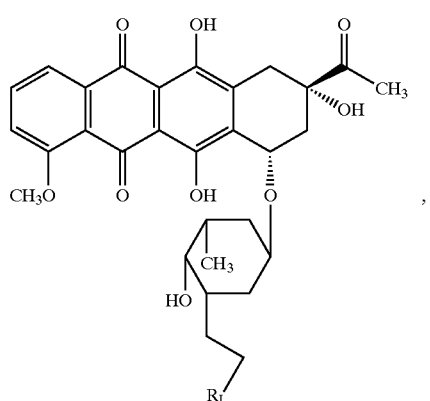
,
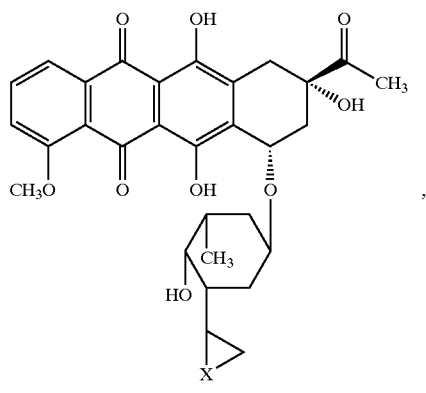
,
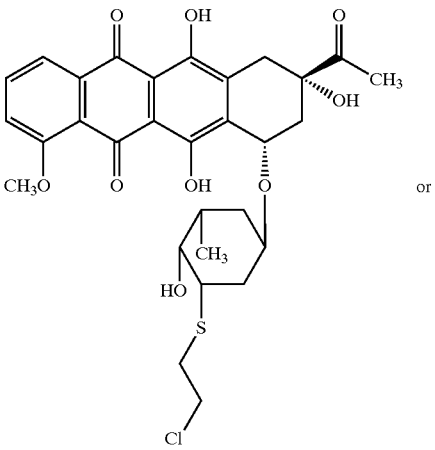
or
-continued
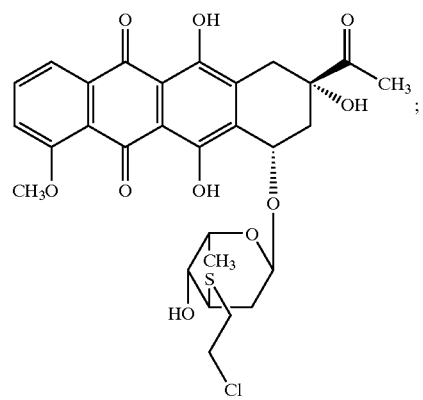
;
wherein $R_L$ is a leaving group selected from the group consisting of I, OMs and OTs, and X is selected from the group consisting of O and NH.
10. The compound of claim 1, wherein said three ring structure is selected from the group consisting of:
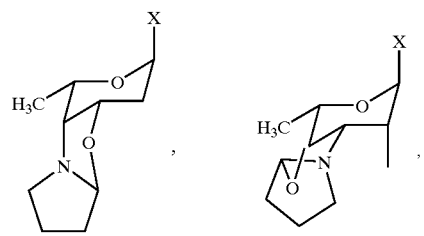
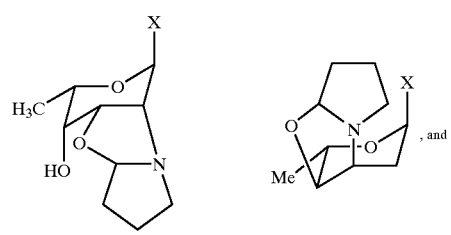
, and
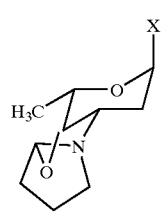
.
wherein X is a glycosidic linkage.

11. The compound of claim 1 having the formula:

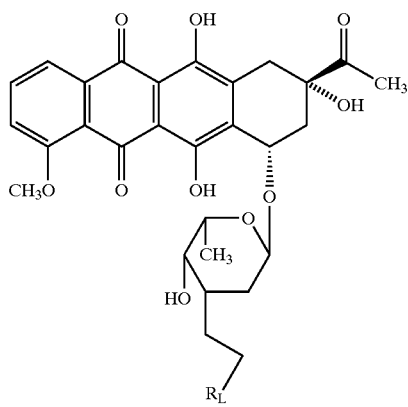

wherein R_L is a leaving group.

12. The compound of claim 1 having the formula:

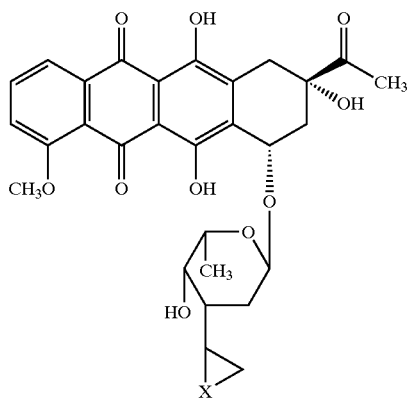

wherein X=O) or NH.

13. The compound of claim 1 having the formula:

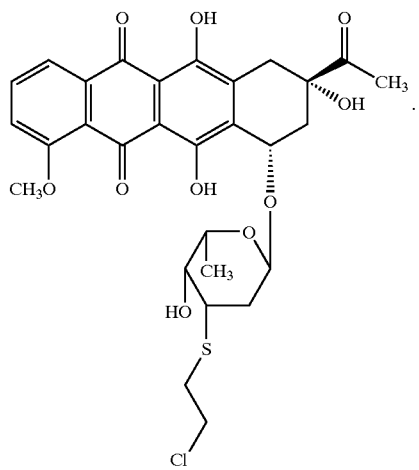

14. The compound of claim 1 having the formula:

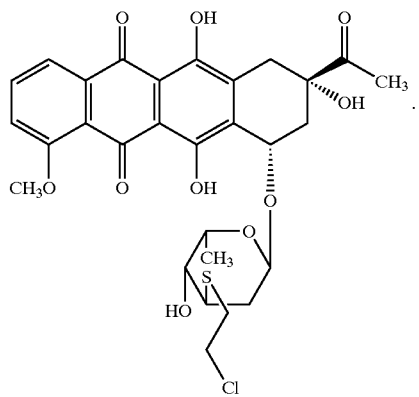

15. The compound of claim 1, wherein at least one of $R^5$ and $R^6$ is independently an ether alkyl group containing an easy leaving group and the easy leaving group is a halogen or sulfonate ester.

* * * * *

UNITED STATES PATENT AND TRADEMARK OFFICE
CERTIFICATE OF CORRECTION

PATENT NO. : 6,437,105 B1
DATED : August 20, 2002
INVENTOR(S) : Waldemar Priebe et al.

It is certified that error appears in the above-identified patent and that said Letters Patent is hereby corrected as shown below:

<u>Column 27,</u>
Line 20, please delete:

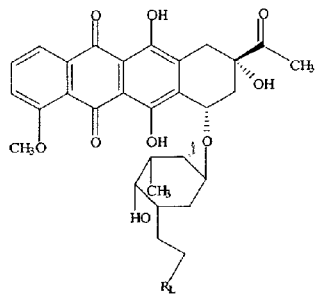

and insert:

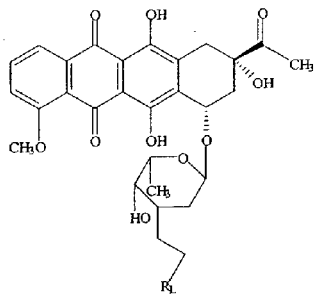

therefor.

<u>Column 28,</u>
Line 30, please delete:

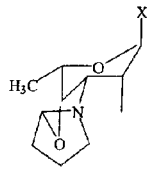

and insert:

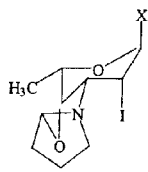

therefor.

UNITED STATES PATENT AND TRADEMARK OFFICE
CERTIFICATE OF CORRECTION

PATENT NO.    : 6,437,105 B1
DATED         : August 20, 2002
INVENTOR(S)   : Waldemar Priebe et al.

It is certified that error appears in the above-identified patent and that said Letters Patent is hereby corrected as shown below:

Column 29,
Line 44, please delete "X=O)" and insert -- X=O -- therefor.

Signed and Sealed this

Twenty-eighth Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,437,105 B1
DATED : August 20, 2002
INVENTOR(S) : Waldemar Priebe et al.

It is certified that error appears in the above-identified patent and that said Letters Patent is hereby corrected as shown below:

Column 27,
Line 20, please delete:

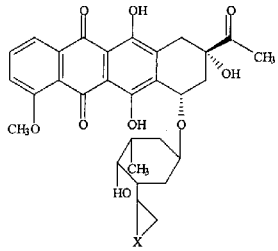

and insert

-- 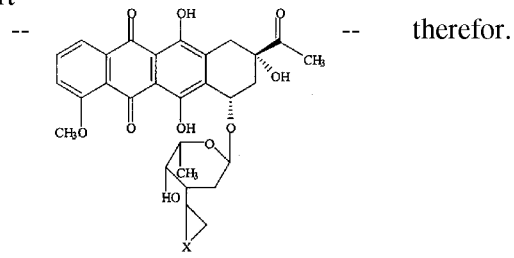 -- therefor.

Signed and Sealed this

Thirteenth Day of July, 2004

JON W. DUDAS
*Acting Director of the United States Patent and Trademark Office*